US008716276B2

(12) United States Patent
Tumey et al.

(10) Patent No.: US 8,716,276 B2
(45) Date of Patent: *May 6, 2014

(54) THIOPHENYL AND PYRROLYL AZEPINES AS SEROTONIN 5-HT$_{2C}$ RECEPTOR LIGANDS AND USES THEREOF

(75) Inventors: L. Nathan Tumey, Pawcatuck, CT (US); David C. Bom, Cincinnati, OH (US); Youssef L. Bennani, Boston, MA (US); Michael J. Robarge, Chagrin Falls, OH (US)

(73) Assignee: Athersys, Inc., Cleveland, OH (US)

( * ) Notice: Subject to any disclaimer, the term of this patent is extended or adjusted under 35 U.S.C. 154(b) by 417 days.

This patent is subject to a terminal disclaimer.

(21) Appl. No.: 13/005,395

(22) Filed: Jan. 12, 2011

(65) Prior Publication Data

US 2011/0112072 A1 May 12, 2011

Related U.S. Application Data

(63) Continuation of application No. 11/654,979, filed on Jan. 17, 2007, now Pat. No. 7,893,051.

(60) Provisional application No. 60/760,240, filed on Jan. 19, 2006.

(51) Int. Cl.
*A61P 25/00* (2006.01)
*A61K 31/55* (2006.01)
*C07D 487/02* (2006.01)
*C07D 223/16* (2006.01)

(52) U.S. Cl.
USPC .......................... 514/215; 540/586; 540/593

(58) Field of Classification Search
USPC .................................. 514/215; 540/586, 593
See application file for complete search history.

(56) References Cited

U.S. PATENT DOCUMENTS

| 4,414,225 A | 11/1983 | Sauter et al. |
| 2002/0123488 A1 | 9/2002 | Binggeli et al. |
| 2006/0003990 A1 | 1/2006 | Bennani et al. |

FOREIGN PATENT DOCUMENTS

| EP | 0 058 341 A1 | 8/1982 |
| EP | 0 324 610 A2 | 7/1989 |
| EP | 0 488 663 A1 | 6/1992 |
| WO | 0224701 A2 | 3/2002 |
| WO | 2006004931 A2 | 1/2006 |

OTHER PUBLICATIONS

Supplemental European Search Report for corresponding European Application No. EP 07 71 8077, Jul. 13, 2010.
J. A. Siuciak et al., "CP-809,101, a selective 5-HT2C agonist shows activity in animal models of antipsychotic activity", Neuropharmacology 52 (2007) 279-290.
L. Zhou et al., "Serotonin 2C Receptor Agonists Improve Type 2 Diabetes via Melanocortin-4 Receptor Signaling Pathways", Cell Metab. Nov. 7, 2007; 6(5): 398-405.
S. M. Grauer et al., "WAY-163909, a 5-HT2C agonist, enhances the preclinical potency of current antipsychotics", Psychopharmacology (2009) 204: 37-48.
D. M. Tomkins et al., "An investigation of the role of 5-HT2C receptors in modifying ethanol self-administration behaviour", Pharmacology, Biochemistry and Behavior 71 (2002) 735-744.
A. J. Grottick et al., "Studies to Investigate the Role of 5-HT2C Receptors on Cocaine- and Food-Maintained Behavior", JPET (2000) vol. 295, No. 3: 1183-1191.
J. CG Halford, "Obesity drugs in clinical development" Current Opinion in Investigational Drugs (2006) 7(4): 312-318.
G. A. Higgins et al., "Serotonin and drug reward: focus on 5-HT2C receptors", European Journal of Pharmacology 480 (2003) 151-162.
M. Isaac, "Serotonergic 5-HT2C Receptors as a Potential Therapeutic Target for the Design Antiepileptic Drugs", Current Topics in Medicinal Chemistry (2005), 5: 59-67.
J. R. Martin et al., "5-HT2C Receptor Agonists: Pharmacological Characteristics and Therapeutic Potential", JPET (1998) vol. 286, No. 2: 913-924.
K. J. Miller, "Serotonin 5-HT2C Receptor Agonists: Potential for the Treatment of Obesity", Molecular Interventions Oct. 2005 vol. 5, Issue 5, 282-291.

*Primary Examiner* — Brenda Coleman
(74) *Attorney, Agent, or Firm* — Wood, Phillips, Katz, Clark & Mortimer

(57) ABSTRACT

The present invention generally relates to a series of compounds, to pharmaceutical compositions containing the compounds, and to use of the compounds and compositions as therapeutic agents. More specifically, compounds of the present invention are thiophenyl and pyrrolyl azepine compounds. These compounds are serotonin receptor (5-HT$_{2c}$) ligands and are useful for treating diseases, disorders, and conditions wherein modulation of the activity of serotonin receptors (5-HT$_{2c}$) is desired (e.g. addiction, anxiety, depression, obesity, and others).

3 Claims, No Drawings

THIOPHENYL AND PYRROLYL AZEPINES AS SEROTONIN 5-HT$_{2C}$ RECEPTOR LIGANDS AND USES THEREOF

CROSS REFERENCE TO RELATED APPLICATION

This application is a continuation application of the U.S. non-provisional application Ser. No. 11/654,979 filed Jan. 17, 2007 which claims the priority of U.S. Provisional Patent Application No. 60/760,240 filed on Jan. 19, 2006, and the disclosure of the both applications is incorporated herein by reference.

FIELD OF THE INVENTION

The present invention generally relates to a series of compounds, to pharmaceutical compositions containing the compounds, and to use of the compounds and compositions as therapeutic agents. More specifically, compounds of the present invention are thiophenyl and pyrrolyl azepine compounds. These compounds are serotonin receptor (5-HT$_{2c}$) ligands and are useful for treating diseases, disorders, and conditions wherein modulation of the activity of serotonin receptors (5-HT$_{2c}$) is desired (e.g. addiction, anxiety, depression, obesity and others).

BACKGROUND OF THE INVENTION

Serotonin has been implicated in a number of diseases, disorders, and conditions that originate in the central nervous system, including diseases, disorders, and conditions related to, for example, sleeping, eating, perceiving pain, controlling body temperature, controlling blood pressure, depression, anxiety, addiction and schizophrenia. Serotonin also plays an important role in peripheral systems, such as the gastrointestinal system, where it has been found to mediate a variety of contractile, secretory, and electrophysiologic effects.

Because of the broad distribution of serotonin within the body, there is a need for drugs that affect serotonergic systems. In particular, agonists, partial agonists, and antagonists of serotonergic systems are of interest for the treatment of a wide range of disorders, including anxiety, depression, hypertension, migraine, obesity, compulsive disorders, schizophrenia, autism, neurodegenerative disorders (e.g., Alzheimer's disease, Parkinsonism, and Huntington's chorea), and chemotherapy-induced vomiting.

The major classes of serotonin receptors (5-HT$_{1-7}$) contain one to seven separate receptors that have been formally classified. See Glennon, et al., *Neuroscience and Behavioral Reviews*, 1990, 14, 35; and D. Hoyer, et al. *Pharmacol. Rev.* 1994, 46, 157-203.

For example, the 5-HT$_2$ family of receptors contains 5-HT$_{2a}$, 5-HT$_{2b}$, and 5-HT$_{2c}$ subtypes, which have been grouped together on the basis of primary structure, secondary messenger system, and operational profile. All three 5-HT$_2$ subtypes are G-protein coupled, activate phospholipase C as a principal transduction mechanism, and contain a seven-transmembrane domain structure. There are distinct differences in the distribution of the three 5-HT$_2$ subtypes in a mammal. The 5-HT$_{2b}$ and 5-HT$_{2a}$ receptors are widely distributed in the peripheral nervous system, with 5-HT$_{2a}$ also found in the brain. The 5-HT$_{2c}$ receptor has been found only in the central nervous system, being highly expressed in many regions of the human brain. See G. Baxter, et al. *Trends in Pharmacol. Sci.* 1995, 16, 105-110.

Subtype 5-HT$_{2a}$ has been associated with effects including vasoconstriction, platelet aggregation, and bronchoconstriction, as well as certain CNS effects, while subtype 5-HT$_2$, has been associated with diseases that include depression, anxiety, obsessive compulsive disorder, addiction, panic disorders, phobias, psychiatric syndromes, and obesity. Very little is known about the pharmocologic role of the 5-HT$_{2b}$ receptor. See F. Jenck, et al., *Exp. Opin. Invest. Drugs*, 1998, 7, 1587-1599; M. Bos, et al., *J. Med. Chem.*, 1997, 40, 2762-2769; J. R. Martin, et al., *The Journal of Pharmacology and Experimental Therapeutics*, 1998, 286, 913-924; S. M. Bromidge, et al., *J. Med. Chem.*, 1998, 41, 1598-1612; G. A. Kennett, *Drugs*, 1998, 1, 4, 456-470; and A. Dekeyne, et al., *Neuropharmacology*, 1999, 38, 415-423.

WO 93/13105, U.S. Pat. Nos. 5,691,330 and 5,532,240 disclose thiophene derivatives; U.S. Pat. No. 4,414,225 discloses thiophene, furan and pyrrole derivatives; U.S. Pat. No. 4,575,504 discloses thienothiazole derivatives; U.S. Pat. No. 5,258,378 discloses certain pyrroloazepine compounds; U.S. Pat. Nos. 4,414,225 and 4,904,653 disclose certain azepine derivatives; WO 2005/019179 discloses certain benzazepines, WO 2005/003096, WO 2005/042490, and WO 2005/042491 disclose benzazepine derivatives; WO 96/11201 discloses furan derivatives; WO 2005/040169 discloses certain fused pyrrole- and pyrazole-containing heterocyclic compounds which are serotonin modulators; WO 2004/024065 discloses substituted bicyclic thiophene derivatives. None of these patents or patent applications disclose compounds of the instant invention.

SUMMARY OF THE INVENTION

The present invention is directed to compounds of the formula:

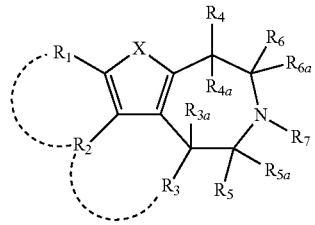

where
X is S or NR$_{11}$;
R$_1$ and R$_2$ are independently selected from the group consisting of H, halogen, C$_{1-8}$ alkyl, C$_{2-8}$ alkenyl, C$_{2-8}$ alkynyl, perhalo alkyl, C$_{1-8}$ alkylperhalo alkyl, —CN, OR$_8$, SR$_8$, —SO$_2$R$_{10}$, —C(=O)R$_{10}$, —C(=O)NR$_8$R$_9$, —NR$_8$CO$_2$R$_{10}$, —SO$_2$NR$_8$R$_9$, —NR$_8$SO$_2$R$_{10}$, aryl or heteroaryl, C$_{1-8}$ alkylaryl or heteroaryl, —C$_{1-8}$ alkyl-O—C$_{1-8}$ alkyl, and —C$_{1-8}$ alkyl-O-aryl or heteroaryl;
R$_1$ and R$_2$ taken together with the atoms to which they are attached can form a 5-7-member carbocycle or heterocycle optionally substituted with up to two substituents selected from alkyl, CF$_3$, and —OR$_8$;
R$_3$ is selected from the group consisting of H, C$_{1-8}$ alkyl, OR$_8$, aryl and heteroaryl;
R$_{3a}$ is H or C$_{1-8}$ alkyl; or R$_3$ and R$_{3a}$ taken together are —CH$_2$CH$_2$—;
R$_2$ and R$_3$ taken together with the atoms to which they are attached form a 5-7-member carbocycle or heterocycle optionally substituted with up to two substituents selected from alkyl, CF$_3$, and —OR$_8$;

$R_4$ is H, $C_{1-8}$ alkyl, or $OR_8$;

$R_{4a}$ is H, $C_{1-8}$ alkyl; or $R_4$ and $R_{4a}$ taken together are —$CH_2CH_2$—;

$R_5$ is selected from the group consisting of H, $C_{1-8}$ alkyl, —$C_{1-8}$ alkyl-O—$C_{1-8}$ alkyl, $C_{1-8}$ alkylaryl or heteroaryl, and —$C_{1-8}$alkyl-O-aryl or heteroaryl;

$R_{5a}$ is H or —$C_{1-8}$ alkyl;

$R_6$ is selected from the group consisting of H, —$C_{1-8}$ alkyl, $C_{1-8}$ alkyl-O—$C_{1-8}$ alkyl, $C_{1-9}$ alkylaryl or heteroaryl, and —$C_{1-8}$alkyl-O-aryl or heteroaryl;

$R_{6a}$ is H or —$C_{1-8}$ alkyl;

$R_7$ is selected from the group consisting of H, —$C_{1-8}$ alkyl, and —$C_{1-8}$alkylaryl or heteroaryl;

$R_8$, $R_9$ are independently selected from the group consisting of H, —$C_{1-8}$ alkyl, —$C_{2-8}$ alkenyl, —$C_{2-8}$ alkynyl, aryl or heteroaryl, —$C_{1-8}$ alkylaryl or heteroaryl, —$C_{1-8}$ alkyl-O—$C_{1-8}$ alkyl, and —$C_{1-8}$ alkyl-O-aryl or heteroaryl;

$R_8$ and $R_9$ taken together with the atom to which they are attached form a 5-7-member heterocycle;

$R_{10}$ is selected from the group consisting of —$C_{1-8}$ alkyl, —$C_{2-8}$ alkenyl, —$C_{2-8}$ alkynyl, aryl or heteroaryl, —$C_{1-8}$ alkylaryl or heteroaryl, —$C_{1-8}$ alkyl-O—$C_{1-8}$ alkyl, and —$C_{1-8}$ alkyl-O-aryl or heteroaryl;

$R_{11}$ is selected from the group consisting of H, —$C_{1-8}$ alkyl, —$C_{1-8}$ alkyl-O—$C_{1-8}$ alkyl, —$SO_2R_{10}$, —$C(=O)R_{10}$, —$C(=O)OR_{10}$, aryl, and heteroaryl, or $C_{1-8}$ alkylaryl or heteroaryl;

$R_{11}$ and $R_1$ together with the atoms to which they are attached may form a 5-7-membered heterocycle optionally substituted with up to two substituents selected from —$C_{1-8}$ alkyl, $CF_3$, and —$OR_8$; and $R_{11}$ and $R_4$ together with the atoms to which they are attached may form a 5-7-membered heterocycle optionally substituted with up to two substituents selected from —$C_{1-8}$ alkyl, $CF_3$, and —$OR_8$;

wherein aryl and heteroaryl are optionally substituted with up to two substituents selected from —$C_{1-8}$ alkyl, halogen, CN, and alkoxy, and the pharmaceutically acceptable salts thereof.

Another embodiment of the present invention provides a pharmaceutical composition comprising a compound of Formula (I), or a pharmaceutically acceptable salt thereof, and a pharmaceutically acceptable carrier.

Still another embodiment of the present invention provides a method of treating a disease, disorder and/or condition in a mammal (e.g., animal or human), wherein a 5-$HT_{2c}$ receptor is implicated and modulation of a 5-$HT_{2c}$ function is desired. The method comprises administering a therapeutically effective amount of a compound of Formula (I), or a pharmaceutically acceptable salt thereof, to the mammal.

Yet another embodiment of the present invention comprises a method of modulating 5-HT receptor function with an effective amount of compound of Formula (I), or a pharmaceutically acceptable salt thereof.

A further embodiment of the present invention provides a method of treating or preventing diseases, disorders, and/or conditions of the central nervous system. The method comprises administering a therapeutically effective amount of a compound of Formula (I), or a pharmaceutically acceptable salt thereof, to the mammal.

Specific diseases, disorders and/or conditions for which compounds of the Formula (I) may have activity include obesity, depression, schizophrenia, anxiety, obsessive compulsive disorder, addiction, panic disorders, sleep disorders, migraine, Type II diabetes, epilepsy, phobias and psychiatric syndromes.

DETAILED DESCRIPTION OF THE INVENTION

The following definitions are used, unless otherwise described:

As used herein, the term "alkyl" includes straight chained and branched hydrocarbon groups containing the indicated number of carbon atoms, typically methyl, ethyl, and straight chain and branched propyl and butyl groups. The term "alkyl" also encompasses cycloalkyl, i.e., a cyclic $C_3$-$C_8$ hydrocarbon group, such as cyclopropyl, cyclobutyl, cyclopentyl, and cyclohexyl. Reference to an individual group or moiety, such as "propyl," embraces only the straight chain group or moiety. A branched chain isomer, such as "isopropyl," is specifically referred to.

The term "alkenyl" as used herein, alone or in combination, refers to a substituted or unsubstituted straight-chain or substituted or unsubstituted branched-chain alkenyl radical containing from 2 to 10 carbon atoms. Examples of such radicals include, but are not limited to, ethenyl, E- and Z-pentenyl, decenyl and the like.

The term "alkynyl" as used herein, alone or in combination, refers to a substituted or unsubstituted straight or substituted or unsubstituted branched chain alkynyl radical containing from 2 to 10 carbon atoms. Examples of such radicals include, but are not limited to, ethynyl, propynyl, propargyl, butynyl, hexynyl, decynyl and the like.

The term "alkoxy" as used herein, alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "halo" is defined herein to include fluoro, chloro, bromo, or iodo. Similarly, the term "halogen" is defined herein to include fluorine, chlorine, bromine, and iodine.

The term "amino", alone or in combination, includes the group —$NH_2$ or —$NR_aR_b$ wherein $R_a$ and $R_b$ are independently hydrogen, alkyl, alkylaryl, or aryl.

The term "aryl," alone or in combination, is defined herein as a monocyclic or bicyclic aromatic group (e.g., phenyl or naphthyl) that can be unsubstituted or substituted, for example, with one or more, and in particular one to three of the following substituents selected from the group consisting of H, halo; CN, $NO_2$, $CF_3$, $N_3$, $C_{1-6}$alkyl, OH, $NR^aR^b$, $OC_{1-6}$ alkyl, $OR^a$, $C(=O)NR^aR^b$, $C(=S)NR^aR^b$, tetrazoyl, triazoyl, amidinyl, guanidinyl, thioguanidinyl, cyanoguanadinyl, and aryl, wherein $R^a$ and $R^b$ are independently hydrogen, alkyl, alkylaryl, or aryl. Generally, "aryl" denotes a phenyl group, or an ortho-fused bicyclic carbocyclic group having nine to ten ring atoms in which at least one ring is aromatic (e.g. naphthyl or tetrahydronaphthyl). The term "aryl" also is abbreviated in the various chemical structures as "Ar."

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfonyl, and alkylsulfonyl. Examples of heteroaryl groups include, but are not limited to, 2H-pyrrolyl, 3H-indolyl, 4H-quinolizinyl, 4H-carbazolyl, acridinyl, benzo[b]thienyl, benzothiazolyl, 13-carbolinyl, carbazolyl, chromenyl, cinnaolinyl, dibenzo[b,d] furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group consisting of non-peroxide oxygen, sulfur, and N(Z) wherein Z is absent or is H, O, $C_{1-4}$alkyl, phenyl or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The term "Het" or "heterocycle" generally represents a heterocyclic group, saturated or partially unsaturated, containing at least one heteroatom selected from the group consisting of oxygen, nitrogen, and sulfur, and optionally substituted with $C_{1-6}$alkyl or $C(=O)OR^6$. Typically "Het" is a monocyclic, bicyclic, or tricyclic group containing one or more heteroatoms selected from the group consisting of oxygen, nitrogen, and sulfur. A "Het" group also can contain an oxo group (=O) attached to the ring. Nonlimiting examples of Het groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

Presently preferred compounds include:
2,2-Dimethyl-1-(3-methyl-5,6,7,8-tetrahydro-4H-thieno[2,3-d]azepin-2-yl)-propan-1-one;
3-Bromo-2-(2,2,2-trifluoro-ethyl)-5,6,7,8-tetrahydro-4H-thieno[2,3-d]azepine;
2-Benzenesulfonyl-5,6,7,8-tetrahydro-4H-thieno[2,3-d]azepine;
(R,S)-2-(2,2,2-Trifluoro-1-methyl-ethyl)-5,6,7,8-tetrahydro-4H-thieno[2,3-d]azepine;
2-Ethanesulfonyl-5,6,7,8-tetrahydro-4H-thieno[2,3-d]azepine;
(R,S)-1-Trifluoromethyl-1,2,3,4,5,6,7,8-octahydro-9-thia-6-aza-cyclopenta[a]azulene;
(R,S)-3,3-Dimethyl-1-trifluoromethyl-1,2,3,4,5,6,7,8-octahydro-9-thia-6-aza-cyclopenta[a]azulene;
2-(2,2,2-Trifluoro-1,1-dimethyl-ethyl)-5,6,7,8-tetrahydro-4H-thieno[2,3-d]azepine;
3-Bromo-4-methyl-2-(2,2,2-trifluoro-ethyl)-5,6,7,8-tetrahydro-4H-thieno[2,3-d]azepine;
2-Ethanesulfonyl-3,4-dimethyl-5,6,7,8-tetrahydro-4H-thieno[2,3-d]azepine;
(R,S)-2,2-Dimethyl-1-(4-methyl-5,6,7,8-tetrahydro-4H-thieno[2,3-d]azepin-2-yl)-propan-1-one;
1-(3-Bromo-4-methyl-5,6,7,8-tetrahydro-4H-thieno[2,3-d]azepin-2-yl)-2,2-dimethyl-propan-1-one;
(R,S)-2-(2,2,2-Trifluoro-ethyl)-4,4a,5,6,7,8-hexahydro-3H-1-thia-6-aza-cyclopenta[cd]azulene;
(R,S)-2-Bromo-3,3-dimethyl-4,4a,5,6,7,8-hexahydro-3H-1-thia-6-aza-cyclopenta[cd]azulene;
(R,S)-2-Bromo-5-methyl-5,6,7,8-tetrahydro-4H-thieno[2,3-d]azepine;
4-Methyl-1-trifluoromethyl-1,2,3,4,5,6,7,8-octahydro-9-thia-6-aza-cyclopenta[a]azulene;
3,3,4-Trimethyl-1-trifluoromethyl-1,2,3,4,5,6,7,8-octahydro-9-thia-6-aza-cyclopenta[a]azulene;
2,2-Dimethyl-1-(5,6,7,8-tetrahydro-4H-thieno[2,3-d]azepin-2-yl)-propan-1-one; and
1-(3-Chloro-5,6,7,8-tetrahydro-4H-thieno[2,3-d]azepin-2-yl)-2,2-dimethyl-propan-1-one.

Certain compounds of the invention may exist in different isomeric (e.g. enantiomers and distereoisomers) forms. The invention contemplates all such isomers both in pure form and in admixture, including racemic mixtures. Enol forms are also included.

The compounds of the invention can exist in unsolvated as well as solvated forms, including hydrated forms, e.g., hemihydrate. In general, the solvated forms, with pharmaceutically acceptable solvents such as water, ethanol, and the like are equivalent to the unsolvated forms for the purposes of the invention.

Certain compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, furmaric, succinic, ascorbic, maleic, methanesulfonic and other mineral carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.*, 66: 1-19 (1977) which is incorporated herein by reference.

As used herein, the term "composition" is intended to encompass a product comprising the specified ingredients in the specified amounts, as well as any product which results, directly or indirectly, from a combination of the specified ingredients in the specified amounts.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfumingagents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, *Pro-drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

The compounds of the present invention may be prepared by the procedures set forth in Schemes 1 through 7. The general analytical conditions set forth after the Schemes were utilized in all examples.

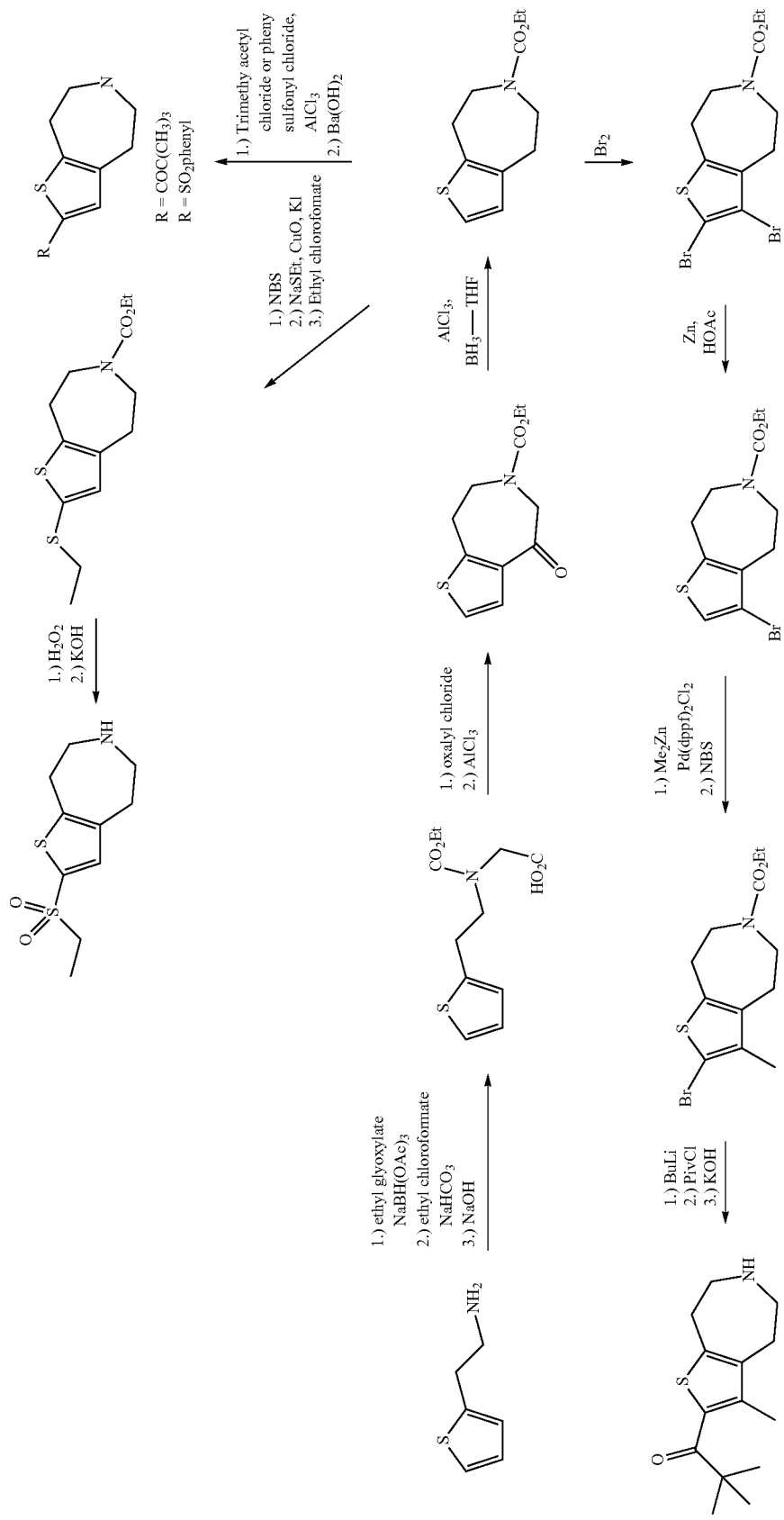
Scheme 1: Synthesis of 2-pivalyl and 2-sulfonyl thiophene azepines

Scheme 2: Synthesis of 2,2,2-trifluoroethyl thiophene azepines
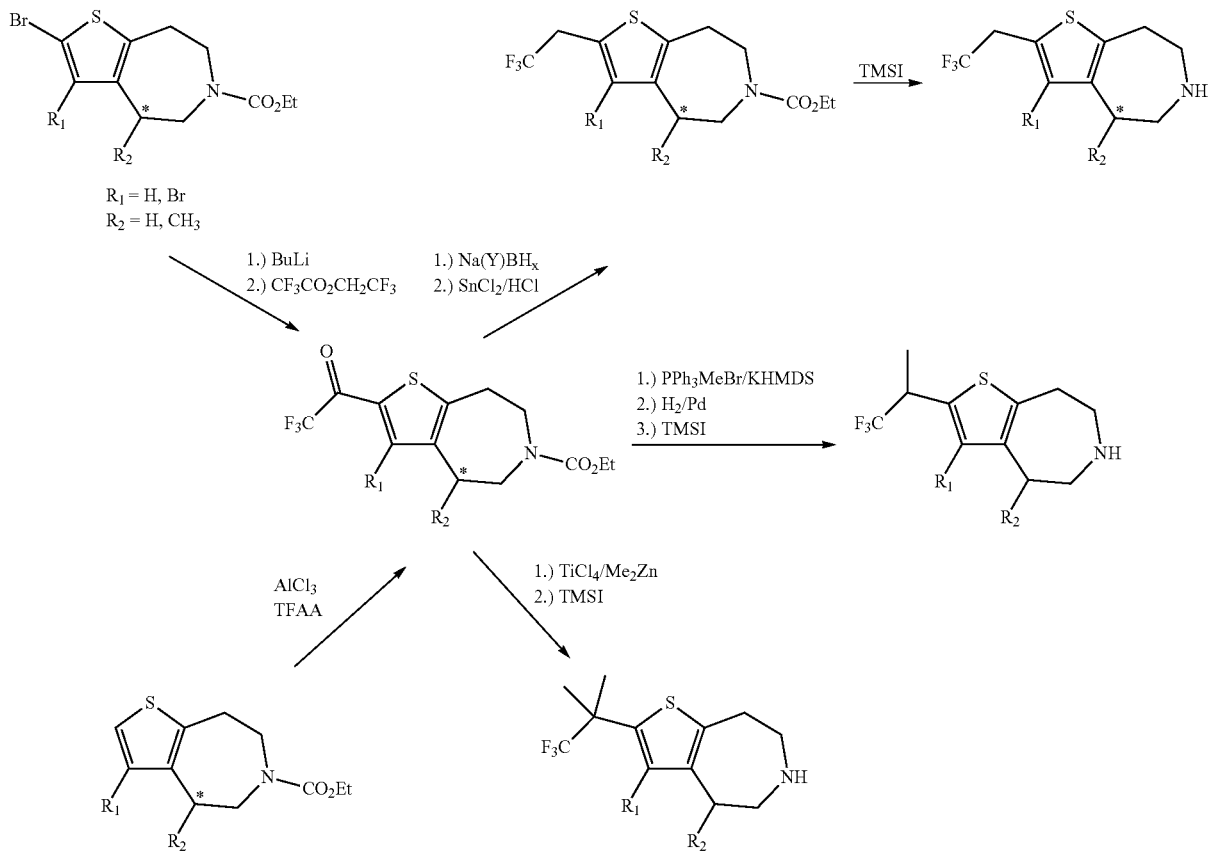
* Denotes that enantiomerically pure material was isolated
Scheme 3: Synthesis of 1-Trifluoromethyl-1,2,3,4,5,6,7,8-octahydro-9-thia-6-aza-cyclopenta[a]azulenes
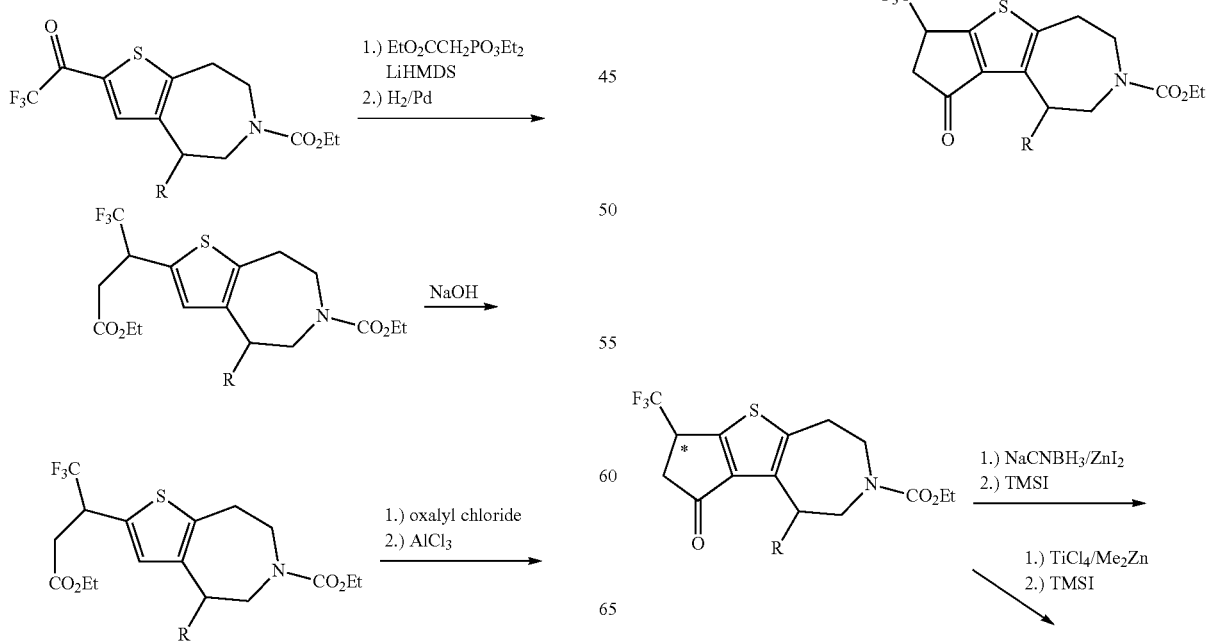

-continued
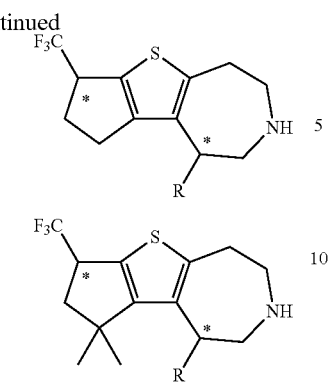
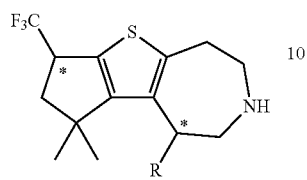
R = H, Me
* Denotes that enantiomerically pure material was isolated

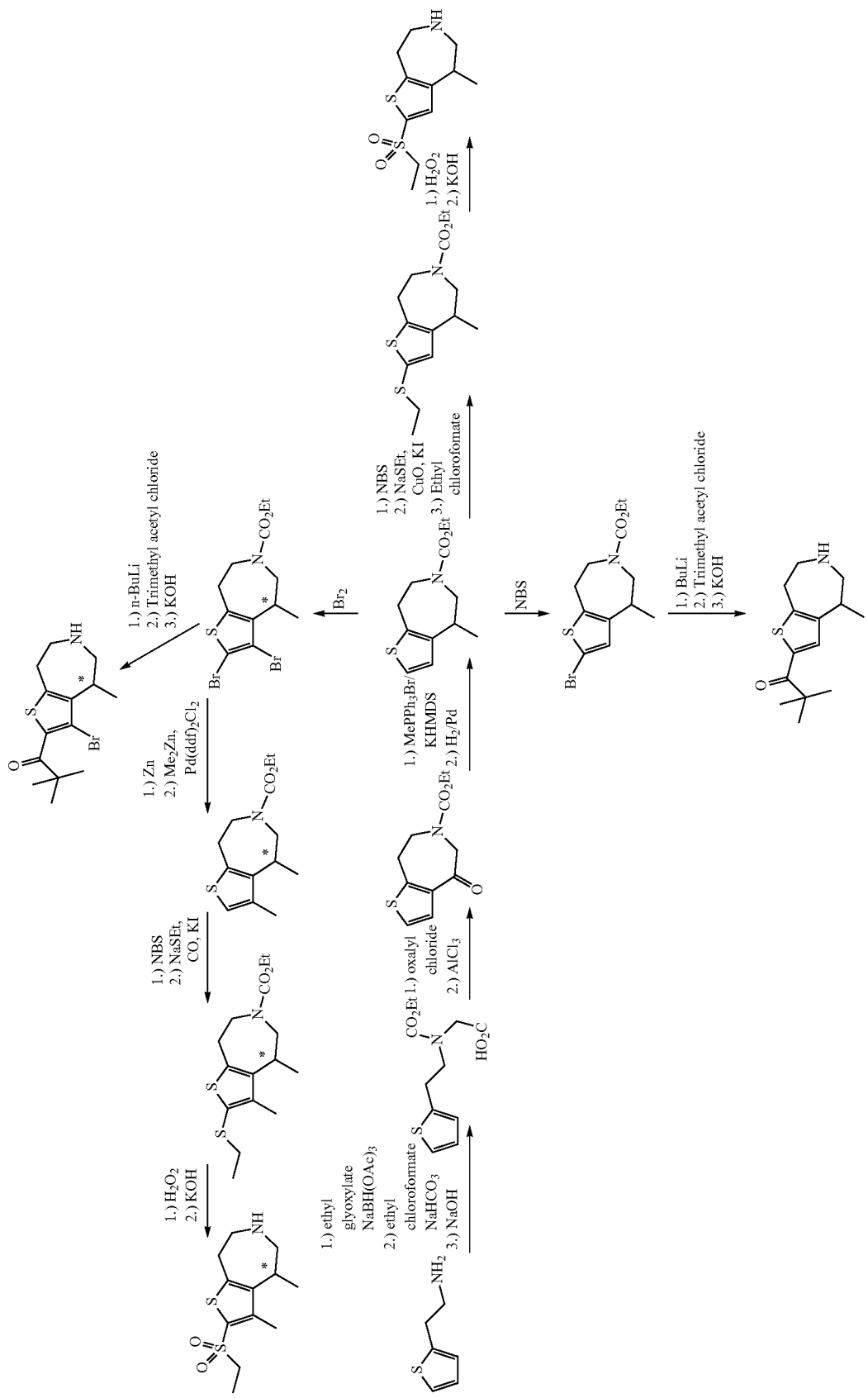
Scheme 4: Synthesis of 4-methyl-5,6,7,8-tetrahydro-4H-thieno[2,3-d]azepines
* Denotes that enantiomerically pure material was isolated

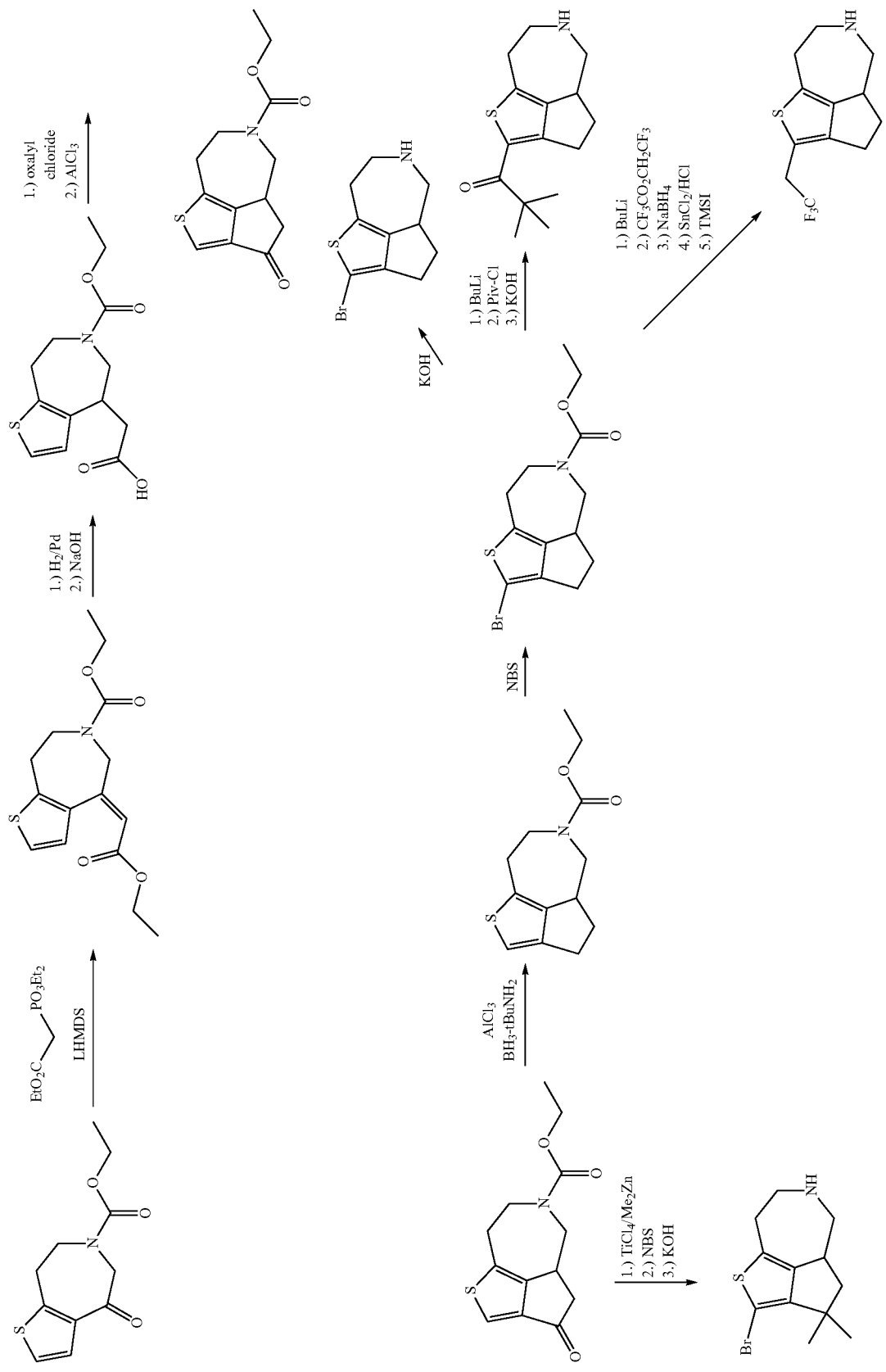

Scheme 6: Synthesis of 5-methyl thienylazapines

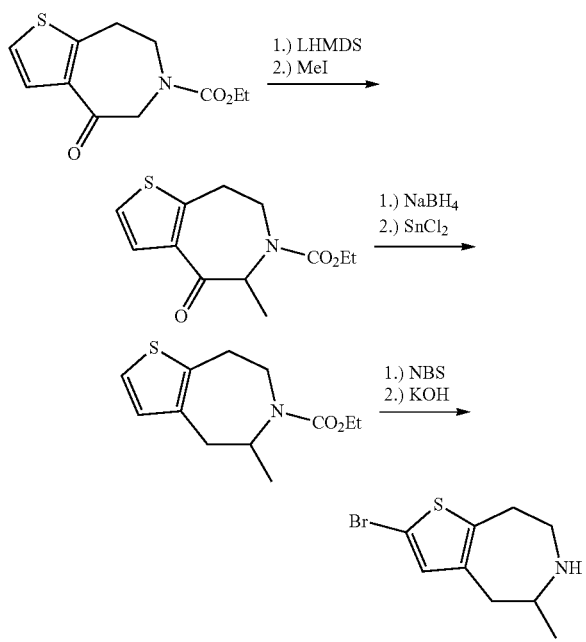

Scheme 7. Synthesis of 2-pivalyl-3-chloro thienylazepine

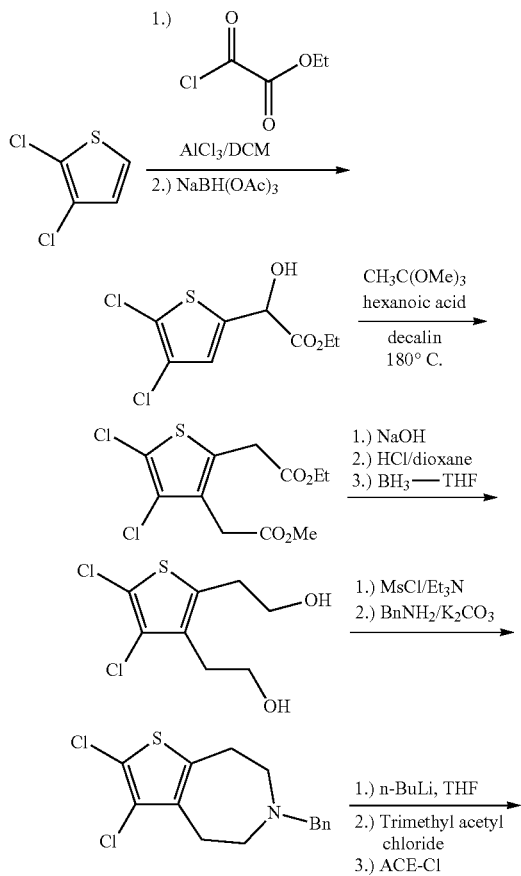

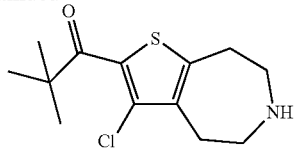

General Analytical Conditions

The following general analytical conditions were utilized in the examples: HPLC analysis and purification was performed using a Waters 2525 binary gradient pump, Waters 2767 sample manager, waters 2487 UV detector (220 and 254 nM), and Waters Micromass ZQ electrospray mass spec detector. The Micromass ZQ was set for both positive and negative ionization (cone voltage=25 and 50, respectively).

Analytical HPLC analysis was performed as follows:
Waters XTerra MS C18 50×4.6 mm 3.5 µm column
Mobile Phase: 10 mM Ammonium Acetate buffer at pH 5.75 and Acetonitrile
Acetonitrile: 10 to 75% at 3.5 minutes, 75 to 99% at 3.9 minutes, 99% hold to 4.2 minutes, 99 to 10% at 4.5 minutes, re-equilibrate.

Preparative HPLC was performed as follows:
Waters XTerra Prep MS C18 50×19 mm 5 µm column
Mobile Phase: 10 mM Ammonium Acetate buffer at pH 5.75 and Acetonitrile
Acetonitrile: 10 to 99% at 8 minutes, 99% hold to 9 minutes, 99 to 10% at 9.5 minutes, re-equilibrate NMR analysis was performed using a Bruker BioSpin UltraShield NMR (300 MHz)

The following examples are illustrative of the preparation of representative compounds of the present invention:

Example 1

2,2-Dimethyl-1-(3-methyl-5,6,7,8-tetrahydro-4H-thieno[2,3-d]azepin-2-yl)-propan-1-one (Scheme 1)

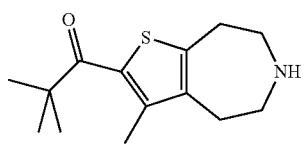 [SMILES: Cc1c(C(=O)C(C)(C)C)sc2c1CCNCC2]

a.) [Ethoxycarbonyl-(2-thiophen-2-yl-ethyl)-amino] acetic acid ethyl ester

2-Thiophen-2-yl-ethylamine (21.0 g, 165 mmol) was stirred in 1 liter of DCM. Ethyl glyoxylate (165 mmol, 50% in toluene) was added followed by 50 uL HOAc. The reaction was stirred for 10 minutes after which time NaBH(OAc)$_3$ (214 mmol, 45 g) was added slowly. After 15 minutes HOAc was added (214 mmol) and the reaction was stirred for 20 minutes. The reaction was concentrated and the crude material was redissolved in 500 mL each of THF and water. NaHCO$_3$ (42 g, 500 mmol) was added followed by ethyl chloroformate (21 mL, 214 mmol). Saturated NaHCO$_3$ was added slowly to the reaction until the gas evolution was minimal. After stirring overnight, the reaction was diluted with EtOAc (400 mL). The product was extracted 2× into EtOAc, dried over MgSO$_4$ and concentrated to the sub-title product as a dark oil.

b.) [Ethoxycarbonyl-(2-thiophen-2-yl-ethyl)-amino]-acetic acid

The crude material from step (a) (165 mmol, ~47 g) was dissolved in EtOH (700 mL) and treated with 600 mL of 1M NaOH. After stirring overnight, the reaction was acidified with concentrated HCl to pH~1. The crude reaction was diluted with EtOAc (400 mL) and washed with water. The water was back-extracted with EtOAc. The combined organic extracts were washed with water (2×) and dried over MgSO$_4$. Concentration and evaporation from toluene (2×) gave the sub-title product as a solid.

c.) 4-Oxo-4,5,7,8-tetrahydro-thieno[2,3-d]azepine-6-carboxylic acid ethyl ester The product of step (b) (~165 mmol, ~42 g) was dissolved in 1 L of DCM. DMF (100 uL) was added followed slowly by oxalyl chloride (21.7 mL, 247 mmol). After 1 hour, the reaction was concentrated to dryness and the crude material was re-dissolved in DCE (1 L). AlCl$_3$ (55 g, 410 mmol) was carefully added and the reaction was stirred at room temperature for ½ hour. The crude reaction was quenched with ice, washed with water (3×), and dried over MgSO$_4$. The title product was purified by silica gel chromatography (30% EtOAc in Hexanes) to give 10.5 grams of the sub-title compound as a white solid. MS: ESI (positive): 240 (M+H).

d.) 4,5,7,8-Tetrahydro-thieno[2,3-d]azepine-6-carboxylic acid ethyl ester

AlCl$_3$ (3.95 g, 29.7 mmol) was added to 50 mL DCM at 0° C. Borane-t-butyl amine complex (5.2 g, 59.5 mmol) was added followed by the product of step (c) (2.37 g, 9.9 mmol) dissolved in DCM (50 mL). The reaction was stirred for 2 hours at room temperature after which time another 3.95 g (29.7 mmol) of AlCl$_3$ was added. After stirring for 10 minutes, the reaction was quenched carefully with 0.1 M HCl (~50 mL). After concentration of the organic solvent, the crude reaction mixture was partitioned between 1M HCl and EtOAc (70 mL each). The aqueous layer was back extracted 1×EtOAc. The combined organic layers were dried over MgSO$_4$ and concentrated. The sub-title product (1.45 g) was obtained after purification by silica gel chromatography (0 to 35% EtOAc in Hexanes). MS: ESI (positive): 226 (M+H).

e.) 2,3-Dibromo-4,5,7,8-tetrahydro-thieno[2,3-d]azepine-6-carboxylic acid ethyl ester The product of step (d) (1.45 g, 6.44 mmol) and NaHCO$_3$ (3.2 g, 38.6 mmol) were stirred in 60 mL cyclohexane. Bromine (1.0 mL, 19.3 mmol) was added slowly and the reaction was stirred in the dark for 15 minutes. The reaction was quenched with 5% Na$_2$SO$_3$ and stirred rapidly for 15 minutes. The sub-title compound was extracted into EtOAc (2×). Drying over MgSO$_4$ and concentration gave the sub-title compound (2.6 g) as a yellow oil.

f.) 3-Bromo-4,5,7,8-tetrahydro-thieno[2,3-d]azepine-6-carboxylic acid ethyl ester The product of step (e) (1.3 g, 3.39 mmol) was dissolved in 1:1 HOAc:water (40 mL), treated with Zn dust (0.44 g, 6.79 mmol), and heated to reflux for 1 hour. The reaction was cooled, diluted with water and extracted 2×EtOAc. The organic extracts were dried over MgSO$_4$ and concentrated to give 0.76 g of the sub-title compound.

g.) 3-Methyl-4,5,7,8-tetrahydro-thieno[2,3-d]azepine-6-carboxylic acid ethyl ester The product of step (f) (375 mg, 1.23 mmol) was dissolved in 4 mL dioxane and treated with Me$_2$Zn (1.25 mL of 2M in toluene) and Pd(dppf)$_2$Cl$_2$. After heating to 100° C. for 3 h, the reaction was cooled, quenched with water, filtered through silica gel (washing with EtOAc), and concentrated to give 337 mg of the sub-title compound as an oil.

h.) 2-Bromo-3-methyl-4,5,7,8-tetrahydro-thieno[2,3-d]azepine-6-carboxylic acid ethyl ester The product of step (g) (337 mg, 1.4 mmol) was dissolve in 10 mL of 1:1 CHCl$_3$:HOAc and treated with NBS (301 mg, 1.7 mmol). After stirring for ½ hour, the reaction was diluted with DCM and washed with water (50 mL) and 1M NaOH (2×50 mL). The crude product was purified by silica gel chromatography to give 235 mg of the sub-title compound.

i.) 2,2-Dimethyl-1-(3-methyl-5,6,7,8-tetrahydro-4H-thieno[2,3-d]azepin-2-yl)-propan-1-one The product of step (h) (60 mg, 0.19 mmol) was dissolve in 2 mL THF and cooled to −78° C. Butyl lithium (0.15 mL of 1.6M) was added and the reaction was stirred for 5 minutes. Trimethylacetyl chloride (36 uL, 0.3 mmol) was added and the reaction was warmed to room temperature. The reaction was quenched with water (5 mL) and the product was extracted into DCM (2×). The extracts were concentrated to dryness and treated with 4 mL of 1:1 EtOH:40% KOH (aq) and heated to 100° C. for 14 hours. The reaction was cooled and diluted with water. The product was extracted into DCM (2×5 mL). The extracts were concentrated and the title compound was purified by preparative HPLC-MS. $^1$H NMR (CD$_3$OD) δ 3.38-3.31 (m, 4H), 3.23 (t, J=5.1 Hz, 2H), 3.04 (t, J=5.2 Hz, 2H), 2.30 (s, 3H), 1.32 (s, 9H); MS: ESI (positive): 252 (M+H).

Example 2

3-Bromo-2-(2,2,2-trifluoro-ethyl)-5,6,7,8-tetrahydro-4H-thieno[2,3-d]azepine (Scheme 2)

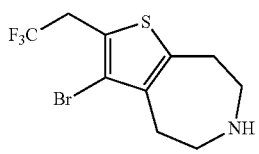 [SMILES: FC(F)(F)Cc1sc2c(c1Br)CCNCC2]

a.) 3-Bromo-2-(2,2,2-trifluoro-acetyl)-4,5,7,8-tetrahydro-thieno[2,3-d]azepine-6-carboxylic acid ethyl ester The product of Example 1, step (e) (200 mg, 0.52 mmol) was dissolved in 5 mL THF, cooled to −78° C. and treated with BuLi (0.33 mL of 1.6 M). After stirring for 15 minutes at −78° C., trifluoroacetyl 2,2,2-trifluoroethanol (132 uL, 0.68 mmol) was added and the reaction was allowed to warm to room temperature. The reaction was quenched with water (50 uL) and concentrated. The residue was purified by silica gel chromatography to give 73 mg of the sub-title compound.

b.) 3-Bromo-2-(2,2,2-trifluoro-ethyl)-4,5,7,8-tetrahydro-thieno[2,3-d]azepine-6-carboxylic acid ethyl ester The product of step (a) (73 mg, 0.18 mmol) was stirred in 3 mL EtOH and treated with $NaBH_4$ (20 mg, 0.5 mmol). After stirring for 20 minutes, the reaction was quenched with HOAc until no bubbling was observed. The reaction was diluted with water (5 mL) and the crude product was extracted into DCM (3×5 mL). The combined organic extracts were concentrated and the residue was dissolved in HOAc (2 mL) and concentrated HCl (1 mL). $SnCl_2$ (225 mg, 1 mmol) was added and the reaction was heated to 80° C. for 2 hours. The crude reaction was diluted with water (10 mL) and the product was extracted into DCM (3×5 mL). The combined organic extracts were concentrated to dryness and used without further purification.

c.) 3-Bromo-2-(2,2,2-trifluoro-ethyl)-5,6,7,8-tetrahydro-4H-thieno[2,3-d]azepine The product of step (b) (0.18 mmol) was dissolved in $CHCl_3$ (3 mL) and treated with TMSI (1 mmol, 200 uL). After heating for ½ hour at 70° C., another 200 uL of TMSI was added and heating was continued for ½ hour. The reaction was cooled and carefully quenched with 0.5 mL each of EtOH and water. The reaction was diluted with 1M NaOH (3 mL) and the product was extracted into DCM (2×5 mL). The organic extracts were concentrated and the residue was purified by preparative HPLC-MS. $^1$H NMR ($CD_3OD$) δ 3.75 (q, J=10.5 Hz, 2H), 3.43-3.34 (m, 4H), 3.26 (t, J=5.4 Hz, 2H), 3.16 (t, J=5.4 Hz, 2H), 3.16 (t, J=5.4 Hz, 2H); MS: ESI (positive): 316, 314 (M+H).

Example 3

2-Benzenesulfonyl-5,6,7,8-tetrahydro-4H-thieno[2,3-d]azepine (Scheme 3)

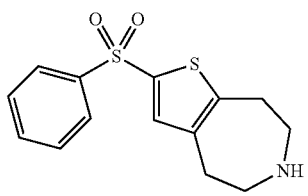 [SMILES: O=S(=O)(c1ccccc1)c1cc2c(s1)CCNCC2]

The product of Example 1, step (d) (75 mg, 0.33 mmol) was dissolved in 2 mL DCE and treated with phenyl sulfonyl chloride (83 uL, 0.66 mmol) followed by $AlCl_3$ (88 mg, 0.66 mmol). After heating to 80° C. for ½ hour, the reaction was cooled and quenched carefully with 1M NaOH. The product was extracted into DCM (2×). The organic extracts were concentrated and the residue was dissolved in 3 mL each EtOH and 40% aqueous KOH. The reaction was heated to 100° C. for 14 hours, cooled, and diluted with water. The title compound was extracted into DCM (2×5 mL) and purified by preparative HPLC-MS. $^1$H NMR ($CD_3OD$) δ 7.96 (d, J=8.1 Hz, 2H), 7.67-7.56 (m, 3H), 5.56 (s, 1H), 3.38-3.32 (m, 4H), 3.27-3.23 (m, 2H), 3.09 (t, J=5.4 Hz, 2H); MS: ESI (positive): 294 (M+H).

Example 4

(R,S)-2-(2,2,2-Trifluoro-1-methyl-ethyl)-5,6,7,8-tetrahydro-4H-thieno[2,3-d]azepine (Scheme 2)

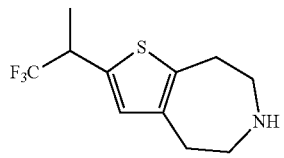 [SMILES: CC(c1cc2c(s1)CCNCC2)C(F)(F)F]

a.) 2-(2,2,2-Trifluoro-acetyl)-4,5,7,8-tetrahydro-thieno[2,3-d]azepine-6-carboxylic acid ethyl ester The product of Example 1, step (d) (410 mg, 1.82 mmol) was dissolved in 20 mL DCE and treated with trifluoroacetic anhydride (510 uL, 3.64 mmol) and $AlCl_3$ (484 mg, 3.64 mmol). The reaction was heated to 50° C. for 2 hours, then cooled and quenched with excess water. The product was extracted into DCM (2×15 mL), dried over $MgSO_4$ and concentrated to give 360 mg of the sub-title compound as a semisolid.

b.) 2-(1-Trifluoromethyl-vinyl)-4,5,7,8-tetrahydro-thieno[2,3-d]azepine-6-carboxylic acid ethyl ester Triphenyl phosphonium bromide (393 mg, 1.1 mmol) was stirred in 7 mL THF. KHMDS (199 mg, 1.0 mmol) was added and the yellow solution was stirred for 30 minutes at room temperature. The product of step (a) (180 mg, 0.56 mmol) was dissolved in 7 mL THF and added to the above reaction. The solution was allowed to stir for 1 hour at room temperature, then diluted with EtOAc (25 mL) and washed with water (2×20 mL). The crude product was purified by silica gel chromatography (30% EtOAc in Hex) to give 100 mg of the sub-title compound.

c.) (R,S)-2-(2,2,2-Trifluoro-1-methyl-ethyl)-4,5,7,8-tetrahydro-thieno[2,3-d]azepine-6-carboxylic acid ethyl ester The product of step (b) (40 mg, 0.12 mmol) was dissolved in 5 mL EtOH and treated with 10 mg of 10% Pd/C (wet, Degussa grade E101). The reaction was stirred rapidly under an atmosphere of hydrogen for 14 hours. Filtration through celite and concentration gave 37 mg of the sub-title compound.

d.) (R,S)-2-(2,2,2-Trifluoro-1-methyl-ethyl)-5,6,7,8-tetrahydro-4H-thieno[2,3-d]azepine The product of step (c) (37 mg, 0.11 mmol) was dissolved in 1 mL $CHCl_3$ and treated with TMSI (47 uL, 0.35 mmol). After heating to 60° C. for 2 hours, the reaction was cooled and concentrated. Purification of the crude residue by preparative HPLC-MS gave the title compound. $^1$H NMR ($CD_3OD$) δ 6.86 (s, 1H), 3.80 (sept., J=7.9 Hz, 1H), 3.39-3.30

(m, 4H), 3.17 (t, J=5.2 Hz, 2H), 3.05 (t, J=5.2 Hz, 2H), 1.48 (d, J=7.2 Hz, 3H); MS: ESI (positive): 250 (M+H).

Example 5

2-Ethanesulfonyl-5,6,7,8-tetrahydro-4H-thieno[2,3-d]azepine (Scheme 1)

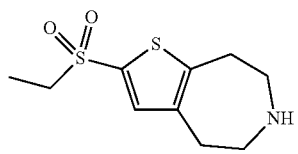

a.) 2-Bromo-4,5,7,8-tetrahydro-thieno[2,3-d]azepine-6-carboxylic acid ethyl ester The product of Example 1, step (d) (80 mg, 0.35 mmol) was dissolved in 2 mL of 1:1 CHCl₃:HOAc and treated with NBS (62 mg, 0.35 mmol). After 15 minutes, the reaction was concentrated to dryness, dissolved in a minimal amount of EtOAc and filtered through a pad of silica gel. The filtrate was evaporated to give 105 mg of the sub-title compound.

b.) 2-Ethylsulfanyl-4,5,7,8-tetrahydro-thieno[2,3-d]azepine-6-carboxylic acid ethyl ester The product of step (a) (105 mg, 0.35 mmol) was dissolved in 1 mL NMP and treated with NaSEt (59 mg, 0.7 mmol), KI (5 mg, 0.03 mmol), and CuO (14 mg, 0.18 mmol). The reaction was heated to 120° C. for 24 hours. Additional NaSEt (59 mg, 0.7 mmol), KI (5 mg, 0.03 mmol), and CuO (14 mg, 0.18 mmol) was added and the heating was continued for 24 hours. The reaction was diluted with water and DCM (~5 mL each) and filtered to remove the dark powdery precipitate. The crude product was extracted into DCM (3×5 mL) and concentrated to ~1 mL. The crude residue was diluted with DCM (2 mL) and treated with Et₃N (140 uL, 1.05 mmol) and ethyl chloroformate (50 uL, 0.52 mmol). After stirring overnight, the reaction was diluted with EtOAc (5 mL) and washed with water (5×) in order to remove the residual NMP. The organic solution was concentrated to give 80 mg of the sub-title compound which was used without further purification.

c.) 2-Ethanesulfonyl-4,5,7,8-tetrahydro-thieno[2,3-d]azepine-6-carboxylic acid ethyl ester The product of step (b) (80 mg, 0.28 mmol) was dissolved in 3 mL HOAc and treated with H₂O₂ (300 uL of 30%, ~3 mmol). After stirring at room temperature for 3 days, the reaction was diluted with EtOAc and washed 4× with water. The organic extract was dried over MgSO₄ and concentrated to give 62 mg of the sub-title compound which was used without further purification.

d.) 2-Ethanesulfonyl-5,6,7,8-tetrahydro-4H-thieno[2,3-d]azepine

The product of step (c) (21 mg, 0.066 mmol) was dissolved in 2 mL EtOH and treated with 2 mL of 40% KOH and subsequently heated to 100° C. in a sealed vessel overnight. The reaction was cooled and diluted with water. The title compound was extracted into DCM (3×) and purified by preparative HPLC-MS. ¹H NMR (CD₃OD) δ 7.47 (s, 1H), 3.25 (q, J=7.2 Hz, 2H), 3.24-3.01 (m, 8H), 1.28 (t, J=7.2 Hz, 3H); MS: ESI (positive): 246 (M+H).

Example 6

(R,S)-1-Trifluoromethyl-1,2,3,4,5,6,7,8-octahydro-9-thia-6-aza-cyclopenta[a]azulene (Scheme 3)

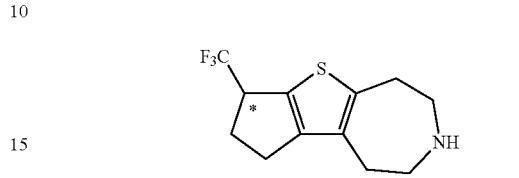

a.) (R,S)-4,4,4-Trifluoro-3-(5,6,7,8-tetrahydro-4H-thieno[2,3-d]azepin-2-yl)-butyric acid Triethylphosphonoacetate (56 mg, 0.25 mmol) and the product of Example 4, step (a) (40 mg, 0.12 mmol) were stirred in 2 mL THF. The reaction was treated with LiHMDS (0.2 mL of 1M) and stirred at room temperature for 1 hour. The reaction was quenched with 5 mL water and the product was extracted into DCM (2×5 mL) and dried over MgSO₄. The organic extract was concentrated to dryness and the residue was dissolved in 5 mL EtOH and treated with ~10 mg of 10% Pd/C (wet, Degussa grade E101). After stirring under hydrogen for 3 days, the reaction was filtered through celite and treated with 1M NaOH (1 mL). After stirring for 2 hours at 60° C., the reaction was diluted with water and the product was extracted into DCM (3×5 mL) to give 45 mg of the sub-title compound which was used without further purification.

b.) (R,S)-3-oxo-1-trifluoromethyl-2,3,4,5,7,8-hexahydro-1H-9-thia-6-aza-cyclopenta[a]azulene-6-carboxylic acid ethyl ester The product of step (a) (45 mg, 0.12 mmol) was dissolved in DCE (2 mL) and treated with oxalyl chloride (43 uL, 0.49 mmol) and 1 drop of DMF. After stirring for 5 minutes at room temperature, the reaction was concentrated to dryness and dissolved in 2 mL DCM. AlCl₃ (66 mg, 0.50 mmol) was added and the reaction was stirred for 5 minutes. The reaction was quenched with water and the crude product was extracted into DCM (2×) to give 32 mg of a dark oil that was used without further purification. The enantiomers of the sub-title compound could be separated using a Chiralpak® AD-RH® 20×250 mm column from Chiral Technologies (MeOH mobile phase) giving enantiomer 1 (reaction time=9.8 minutes) and enantiomer 2 (reaction time=11.5 minutes).

c.) (R,S)-1-Trifluoromethyl-1,2,3,4,5,6,7,8-octahydro-9-thia-6-aza-cyclopenta[a]azulene The product of step (b) (racemic, 32 mg, 0.10 mmol) was dissolved in DCE (1 mL) and treated with ZnI₂ (64 mg, 0.2 mmol) and NaCNBH₃ (44 mg, 0.7 mmol). A thick slurry formed after stirring overnight. The reaction was filtered and the solid was washed with DCM. The combined filtrates were washed with water (1×5 mL) and concentrated to dryness. The residue was dissolved in CHCl₃ (2 mL) and treated with TMSI (70 uL, 0.5 mmol). After heading to 60° C. for 1 hour, an additional 50 uL of TMSI was added and heating was continued for 14 hours. The reaction was cooled, concentrated to dryness, and purified by preparative HPLC-MS to give the title compound. $^1$H NMR (CD$_3$OD) δ 4.02-3.97 (m, 1H), 3.40-3.33 (m, 4H), 3.18 (t, J=5.2 Hz, 2H), 2.97 (t, J=5.4 Hz, 2H), 2.83-2.65 (m, 3H), 2.57-2.47 (m, 1H); MS: ESI (positive): 262 (M+H).

Example 7

(R,S)-3,3-Dimethyl-1-trifluoromethyl-1,2,3,4,5,6,7,8-octahydro-9-thia-6-aza-cyclopenta[a]azulene (Scheme 3)

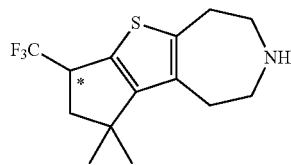 [SMILES: CC1(C)CC(C(F)(F)F)c2sc3c(c21)CCNCC3]

a.) (R,S)-3,3-Dimethyl-1-trifluoromethyl-2,3,4,5,7,8-hexahydro-1H-9-thia-6-aza-cyclopenta[a]azulene-6-carboxylic acid ethyl ester DCM (3 mL) was cooled to −78° C. and treated with TiCl$_4$ (190 uL, 1.73 mmol) followed by Me$_2$Zn (0.86 mL of 2M in toluene). After stirring the dark red suspension at −78° C. for 15 minutes, the product of example 6, step (b) (racemic, 100 mg, 0.29 mmol) was added as a solution in 3 mL DCM. The reaction was warmed to 0° C. and stirred for 3 hours. The solution was poured over ice and the product was extracted into DCM (2×10 mL). The organic extract was dried over MgSO$_4$ and concentrated to give 84 mg of the sub-title compound, which was used without further purification.

b.) (R,S)-3,3-Dimethyl-1-trifluoromethyl-1,2,3,4,5,6,7,8-octahydro-9-thia-6-aza-cyclopenta[a]azulene The product of step a) (37 mg, 0.10 mmol) was dissolved in CHCl$_3$ (2 mL) and treated with TMSI (1 mmol, 140 uL). After heating to 60° C. for 2 hours, the reaction was quenched with MeOH and concentrated to dryness. The title compound was obtained after purification of the crude residue by preparative HPLC-MS. $^1$H NMR (CD$_3$OD) δ 4.09-3.94 (m, 1H), 3.41-3.32 (m, 4H), 3.17 (t, J=5.2 Hz, 2H), 3.08 (t, J=5.2 Hz, 2H), 2.53 (dd, J=9, 13.5 Hz, 1H), 2.31 (dd, J=6.6, 13.8 Hz, 1H), 1.39 (s, 3H), 1.31 (s, 3H); MS: ESI (positive): 290 (M+H).

Example 8

2-(2,2,2-Trifluoro-1,1-dimethyl-ethyl)-5,6,7,8-tetrahydro-4H-thieno[2,3-d]azepine (Scheme 2)

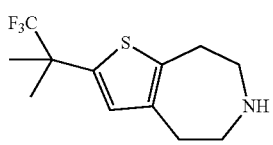

a.) 2-(2,2,2-Trifluoro-1,1-dimethyl-ethyl)-4,5,7,8-tetrahydro-thieno[2,3-d]azepine-6-carboxylic acid ethyl ester DCM (2 mL) was cooled to −78° C. and treated with TiCl$_4$ (82 uL, 0.75 mmol) followed by Me$_2$Zn (370 uL to 2 M). After stirring for 15 minutes at −78° C., the product of example 4, step (a) (40 mg, 0.125 mmol) was added as a solution in 3 mL DCM. The reaction was warmed to 0° C. for 1 hour then to room temperature for 6 hours. The reaction was quenched over ice and extracted into DCM (2×5 mL). The organic extracts were dried over MgSO$_4$ and concentrated to give 34 mg of the sub-title compound which was used without further purification.

b.) 2-(2,2,2-Trifluoro-1,1-dimethyl-ethyl)-5,6,7,8-tetrahydro-4H-thieno[2,3-d]azepine The product of step (a) (34 mg, 0.1 mmol) was dissolved in 2 mL CHCl$_3$ and treated with TMSI (140 uL, 1 mmol). After heating to 60° C. for 2 hours, the reaction was concentrated to dryness and the title compound was purified by preparative HPLC-MS. $^1$H NMR (CD$_3$OD) δ 6.91 (s, 1H), 3.39-3.32 (m, 4H), 3.21-3.17 (m, 2H), 3.09-3.05 (m, 2H), 1.55 (s, 6H); MS: ESI (positive): 264 (M+H).

Example 9

3-Bromo-4-methyl-2-(2,2,2-trifluoro-ethyl)-5,6,7,8-tetrahydro-4H-thieno[2,3-d]azepine (Scheme 2)

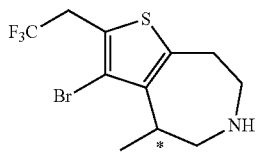

a.) 4-Methylene-4,5,7,8-tetrahydro-thieno[2,3-d]azepine-6-carboxylic acid ethyl ester Methyl triphenylphosphonium bromide (6.3 g, 17.6 mmol) was dissolved in 150 mL THF and cooled to 0° C. KHMDS (3.2 g, 16.2 mmol) was added portionwise and the reaction was stirred for ½ hour. The product of Example 1, step (c) (3.0 g, 12.5 mmol) was added as a solution in 25 mL THF. The reaction was warmed to room temperature and stirred for 1 hour. The mixture was concentrated and the title product was purified by silica gel chromatography (0% to 40% EtOAc in hexanes) to give 2.6 g of the sub-title compound.

b.) (R,S)-4-Methyl-4,5,7,8-tetrahydro-thieno[2,3-d]azepine-6-carboxylic acid ethyl ester The product of step (a) was dissolved in 100 mL EtOH and treated with 0.5 g of 10% Pd/C (wet, Degussa type E101). After stirring rapidly for 14 hours under an atmosphere of hydrogen, the reaction was filtered through celite and concentrated to give 2.3 g of the sub-title compound as a clear oil. MS: ESI (positive): 240 (M+H).

c.) 2,3-Dibromo-4-methyl-4,5,7,8-tetrahydro-thieno[2,3-d]azepine-6-carboxylic acid ethyl ester The product of step (b) (5.6 g, 23.4 mmol) was dissolved in 250 mL cyclohexane and treated with NaHCO₃ (11.8 g, 140 mmol). Bromine (3.6 mL, 70.3 mmol) was added slowly and the reaction was stirred for ½ hour at room temperature after which time it was quenched with Na₂SO₃ (180 mL of 5% aqueous). After stirring rapidly for 15 minutes, EtOAc was added (~100 mL) and the organic layer was removed and dried over MgSO₄ to give the sub-title compound. The two enantiomers were separated using a Chiralpak® AD-RH® 20×250 mm column from Chiral Technologies (10 mL/min MeOH mobile phase) to give enantiomer 1 (reaction time=9.8 minutes) and enantiomer 2 (reaction time=11.4 minutes) of the subtitle compound.

d.) 3-Bromo-4-methyl-2-(2,2,2-trifluoro-acetyl)-4,5,7,8-tetrahydro-thieno[2,3-d]azepine-6-carboxylic acid ethyl ester The product of step (c) (enantiomer 2, 60 mg, 0.15 mmol) was dissolved in 2 mL dry THF and cooled to −78° C. Butyl lithium (0.11 mL of 1.6 M) was added and the solution was stirred for 5 minutes then quenched with trifluoroacetyl 2,2,2-trifluoroethanol (50 uL, 0.24 mmol). After warming to room temperature, the reaction was filtered through a pad of silica gel (washing with EtOAc). The filtrate was evaporated to give 62 mg of the sub-title compound that was used without further purification.

e.) 3-Bromo-4-methyl-2-(2,2,2-trifluoro-ethyl)-4,5,7,8-tetrahydro-thieno[2,3-d]azepine-6-carboxylic acid ethyl ester The product of step (d) (62 mg, 0.15 mmol) was dissolved in 2 mL EtOH and treated with NaBH₄ (0.6 mmol). After 15 minutes, the reaction was quenched with HOAc till the bubbling ceased and diluted with water. The product was extracted into DCM (2×5 mL), dried over MgSO₄ and concentrated. The crude residue was dissolved in 3 mL of 1:1 HOAc:concentrated HCl and treated with SnCl₂ (225 mg, 1 mmol). The reaction was heated to 70° C. for 1 hour and then stirred at room temperature for 3 days. The reaction was diluted with EtOAc (10 mL) and washed with water (2×) and 1M NaOH (2×). The organic solution was concentrated to dryness giving 40 mg of the sub-title compound that was used without further purification.

f.) 3-Bromo-4-methyl-2-(2,2,2-trifluoro-ethyl)-5,6,7,8-tetrahydro-4H-thieno[2,3-d]azepine The product of step (e) (40 mg, 0.10 mmol) was deprotected and purified according to the procedure described for Example 2, step (c). ¹H NMR (CD₃OD) δ 3.75 (q, J=10.4 Hz, 2H), 3.63-3.55 (m, 3H), 3.42-3.31 (m, 2H), 3.24-3.15 (m, 2H), 1.35 (d, J=7.2 Hz, 3H); MS: ESI (positive): 328, 330 (M+H).

Example 10

2-Ethanesulfonyl-3,4-dimethyl-5,6,7,8-tetrahydro-4H-thieno[2,3-d]azepine (Scheme 4)

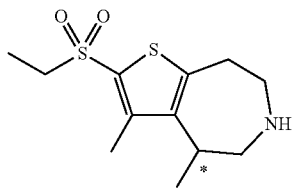 [SMILES: CCS(=O)(=O)c1sc2c(c1C)C(C)CNCC2]

a.) 3-Bromo-4-methyl-4,5,7,8-tetrahydro-thieno[2,3-d]azepine-6-carboxylic acid ethyl ester The product of Example 9, step (c) (enantiomer 2, 0.75 g, 1.9 mmol) and Zn (0.25 g, 3.8 mmol) were heated to reflux in 20 mL each water and HOAc. After ½ hour, the reaction was cooled, diluted with EtOAc, and washed 2× with water. The organic layer was dried over MgSO₄ and concentrated to give 490 mg of the sub-title compound as an oil.

b.) 3,4-Dimethyl-4,5,7,8-tetrahydro-thieno[2,3-d]azepine-6-carboxylic acid ethyl ester The product of step (a) (150 mg, 0.47 mmol) was dissolved in 3 mL dioxane and treated with Me₂Zn (0.47 mL of 2M in toluene) and Pd(ddf)₂Cl₂ (11 mg, 0.014 mmol). After heating to 100° C. for 3 hours, the reaction was quenched with water and filtered. The filtrate was partitioned between EtOAc and water (7 mL each). The organic layer was dried over MgSO₄ and concentrated to give 92 mg of the sub-title compound, which was used without further purification.

c.) 2-Bromo-3,4-dimethyl-4,5,7,8-tetrahydro-thieno[2,3-d]azepine-6-carboxylic acid ethyl ester The product of step (b) (92 mg, 0.36 mmol) was dissolved in 4 mL of 1:1 HOAc/CHCl₃ and treated with NBS (67 mg, 0.38 mmol). After stirring for ½ hour, the reaction was diluted with EtOAc (70 mL) was washed with water (3×30 mL) and 1M NaOH (2×30 mL). The organic solution was dried over MgSO₄ and concentrated. The crude product was purified by silica gel chromatography (EtOAc/Hex) to give 90 mg of the sub-title compound.

d.) 2-Ethylsulfanyl-3,4-dimethyl-4,5,7,8-tetrahydro-thieno[2,3-d]azepine-6-carboxylic acid ethyl ester The product of step (c) (60 mg, 0.18 mmol) was dissolved in 2 mL NMP and treated with NaSEt (45 mg, 0.54 mmol), KI (3 mg, 0.018 mmol), and CuO (7 mg, 0.09 mmol). After heating for 2 days at 120° C., an additional quantity of NaSEt (45 mg, 0.54 mmol), KI (3 mg, 0.018 mmol), and CuO (7 mg, 0.09 mmol) was added and heating was continued for 3 days. The reaction was diluted with 2 mL each of DCM and water. The resulting black precipitate was filtered and discarded. The filtrate was evaporated to dryness under vacuum, then diluted with DCM (4 mL) and treated with Et₃N (111 uL, 0.8 mmol) and ethyl chloroformate (70 uL, 0.7 mmol). After stirring for ½ hour, the reaction was diluted with DCM (5 mL) and washed with water (2×5 mL). Concentration of the organic layer gave approximately 55 mg of the sub-title compound, which was used without further purification.

e.) 2-Ethanesulfonyl-3,4-dimethyl-5,6,7,8-tetrahydro-4H-thieno[2,3-d]azepine

The product of step (d) (55 mg, 0.17 mmol) was dissolved in 2 mL HOAc and treated with 30% H$_2$O$_2$ (220 uL, 2 mmol). After heating to 70° C. for 1 hour, the reaction was diluted with water (8 mL) and the product was extracted into DCM (3×5 mL). The crude reside was dissolved in 4 mL of 1:1 EtOH:40% KOH (aq) and heated to 100° C. for 14 hours. The reaction was cooled and diluted with water. The product was extracted into DCM (2×5 mL) and purified by preparative HPLC-MS to give the title compound. $^1$H NMR (CD$_3$OD) δ 3.64-3.19 (m, 7H), 3.25 (q, J=7.5 Hz, 2H), 2.44 (s, 3H), 1.36 (d, J=7.2 Hz, 3H), 1.27 (t, J=7.4 Hz, 3H); MS: ESI (positive): 274 (M+H).

Example 11

(R,S)-2,2-Dimethyl-1-(4-methyl-5,6,7,8-tetrahydro-4H-thieno[2,3-d]azepin-2-yl)-propan-1-one (Scheme 4)

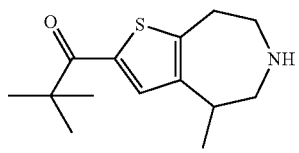 [SMILES: CC1CNCCc2sc(C(=O)C(C)(C)C)cc21]

a.) (R,S)-2-Bromo-4-methyl-4,5,7,8-tetrahydro-thieno[2,3-d]azepine-6-carboxylic acid ethyl ester The product of Example 9, step (b) (racemic, 80 mg, 0.35 mmol) was dissolved in 2 mL of 1:1 CHCl$_3$/HOAc. N-Bromo-succinamide (62 mg, 0.35 mmol) was added and the reaction was stirred for 15 minutes. Concentration and purification by silica gel chromatography gave the sub-title compound as a yellow oil.

b.) (R,S)-2,2-Dimethyl-1-(4-methyl-5,6,7,8-tetrahydro-4H-thieno[2,3-d]azepin-2-yl)-propan-1-one The product of step (a) (55 mg, 0.17 mmol) was dissolved in THF (2 mL) and cooled to −78° C. Butyl lithium (0.16 mL of 1.6M) was added and the reaction was stirred for 15 minutes. After quenching with trimethyl acetyl chloride (41 uL, 0.34 mmol) the reaction was warmed to room temperature and concentrated. The crude residue was dissolved in 2 mL EtOH and treated with 2 mL of 40% KOH (aq). After heating overnight to 100° C., the reaction was cooled and diluted with water. The product was extracted into DCM (2×) and the title compound was purified by preparative HPLC-MS. $^1$H NMR (CD$_3$OD) δ 7.69 (s, 1H), 3.51-3.12 (m, 7H), 1.46 (d, J=7.2; H, 3H), 1.36 (s, 9H); MS: ESI (positive): 252 (M+H).

Example 12

1-(3-Bromo-4-methyl-5,6,7,8-tetrahydro-4H-thieno[2,3-d]azepin-2-yl)-2,2-dimethyl-propan-1-one (Scheme 4)

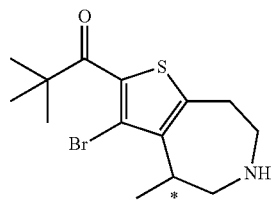 [SMILES: CC1CNCCc2sc(C(=O)C(C)(C)C)c(Br)c21]

a.) 3-Bromo-2-(2,2-dimethyl-propionyl)-4-methyl-4,5,7,8-tetrahydro-thieno[2,3-d]azepine-6-carboxylic acid ethyl ester The product of Example 9, step (c) (enantiomer 2, 200 mg, 0.50 mmol) was dissolved in 5 mL THF and cooled to −78° C. Butyl lithium (0.31 mL of 1.6M) was added and the reaction was stirred for 15 minutes. After quenching with trimethyl acetyl chloride (90 uL, 0.75 mmol) the reaction was warmed to room temperature and concentrated. Purification of the crude residue by silica gel chromatography gave 170 mg of the sub-title compound.

b.) 1-(3-Bromo-4-methyl-5,6,7,8-tetrahydro-4H-thieno[2,3-d]azepin-2-yl)-2,2-dimethyl-propan-1-one The product of step (a) (56 mg, 0.14) was stirred in 2 mL CHCl$_3$ and treated with TMSI (57 uL, 0.42 mmol). After heating to 70° C. for 1 hour, another 0.42 mmol of TMSI was added and the heating was continued for 1 hour. The reaction was cooled and partitioned between 1M NaOH and CHCl$_3$. The organic layer was concentrated and purified by HPLC-MS gave the title compound. $^1$H NMR (CD$_3$OD) δ 3.74-3.56 (m, 4H), 3.43-3.20 (m, 3H), 1.35 (d, J=7.2 Hz, 3H), 1.30 (s, 9H); MS: ESI (positive): 330, 332 (M+H).

Example 13

(R,S)-2-(2,2,2-Trifluoro-ethyl)-4,4a,5,6,7,8-hexahydro-3H-1-thia-6-aza-cyclopenta[cd]azulene (Scheme 5)

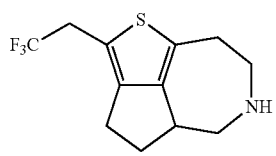 [SMILES: FC(F)(F)Cc1sc2c3c1CCC3CNCC2]

a.) (E,Z)-4-Ethoxycarbonylmethylene-4,5,7,8-tetrahydro-thieno[2,3-d]azepine-6-carboxylic acid ethyl ester A 1.6M LHMDS solution in THF (15 mL) was added to the product from Example 1, step (c) (2.0 g, 8.37 mmol) and triethyl phosphonoacetate (4 mL, 16.74 mmol) in anhydrous THF (100 mL). The reaction was stirred at room temperature overnight then treated with additional LHMDS solution (3.2 mL of 1.6 M) and triethylphosphonoacetate (800 µL, 3.3 mmol). After stirring for 3 hours, the reaction was quenched with water and diluted with DCM. The organic layer was dried over MgSO$_4$ and concentrated to give the sub-title compound, which was used without further purification. MS: ESI (positive): 310 (M+H).

b.) (R,S)-4-Ethoxycarbonylmethyl-4,5,7,8-tetrahydro-thieno[2,3-d]azepine-6-carboxylic acid ethyl ester The product of step (a) (2.47 g, 8 mmol) was stirred with 2.0 g of 10% Pd/C (wet, Degussa grade E101) in methanol (8 mL) under H$_2$ (1 atm) for 72 hours. The reaction was filtered over celite and concentrated to dryness to give the sub-title compound as an oil, which was used without further purification. MS: ESI (positive): 312 (M+H).

c.) (R,S)-4-Carboxymethyl-4,5,7,8-tetrahydro-thieno[2,3-d]azepine-6-carboxylic acid ethyl ester The product of step (b) (2.47 g, 8 mmol) was stirred in ethanol (60 mL) with 1M NaOH (30 mL) at ambient temperature overnight. The reaction acidified with 1M HCl and partitioned between DCM and water. The organic layer was washed with water, dried over MgSO$_4$, and concentrated to dryness to give the 2.13 g of the sub-title compound as a yellow oil. MS: ESI (positive): 284 (M+H).

d.) (R,S)-3-oxo-3,4,4a,5,7,8-hexahydro-1-thia-6-aza-cyclopenta[cd]azulene-6-carboxylic acid ethyl ester Oxalyl chloride (3 mL, 37.7 mmol) and a catalytic amount of DMF were added to a solution of the product from step c) (2.13 g, 7.54 mmol) in DCM (40 mL) and the reaction was stirred at ambient temperature for 1 hour. The reaction was concentrated to dryness and redissolved in dichloroethane (100 mL). AlCl$_3$ (2.0 g, 15.1 mmol) was added to the solution and the reaction was stirred at ambient temperature overnight. The reaction was quenched with ice and partitioned between DCM and water. The organic layer was concentrated to give the sub-title compound, which was purified by chromatography (EtOAc/Hex, isolated 1.02 g) prior to use in subsequent steps. MS: ESI (positive): 266 (M+H).

e.) (R,S)-3,4,4a,5,7,8-Hexahydro-1-thia-6-aza-cyclopenta[cd]azulene-6-carboxylic acid ethyl ester AlCl$_3$ (627 mg, 4.72 mmol) was added to BH$_3$tBuNH$_2$ (492 mg, 5.66 mmol) in DCM (2 mL) at 0° C. The solution was stirred for 10 minutes then treated with the product from step (d) (250 mg, 0.943 mmol) as a solution in DCM (1 mL). After warming to room temperature, the reaction was quenched with 0.1M HCl dropwise and concentrated to dryness. The reaction was diluted in 1M HCl and extracted into EtOAc. The organic layer was concentrated to give the sub-title compound, which was purified by chromatography (EtOAc/Hex) prior to use in subsequent steps. MS: ESI (positive): 252 (M+H).

f.) (R,S)-2-Bromo-3,4,4a,5,7,8-hexahydro-1-thia-6-aza-cyclopenta[cd]azulene-6-carboxylic acid ethyl ester The sub-title compound was prepared by the method of Example 1, step (h) using the product from step (e) and was used in crude form without purification.

g.) (R,S)-2-(2,2,2-Trifluoro-acetyl)-3,4,4a,5,7,8-hexahydro-1-thia-6-aza-cyclopenta[cd]azulene-6-carboxylic acid ethyl ester A solution of 1.6M nBuLi in hexane (130 µL) was added to a solution of the product of step f) (69 mg, 0.208 mmol) in anhydrous THF (mL) at −78° C. and stirred for 15 minutes. Trifluoro-acetic acid 2,2,2-trifluoro-ethyl ester (50 µL, 0.270 mmol) was added and the reaction was warmed to ambient temperature. The reaction was quenched with water, extracted into ethyl acetate and the organic layers were combined and concentrated. Trifluoroacetic anhydride (750 µA, 5.36 mmol) and AlCl$_3$ (600 mg, 4.51 mmol) were added to a solution of the crude product in dichloroethane (10 mL) and the reaction was heated to 80° C. overnight. The reaction was cooled to ambient temperature, quenched with water and extracted into DCM. The organic layer was concentrated to give the sub-title compound that was used in crude form without purification. MS: ESI (positive): 348 (M+H).

h.) (R,S)-2-(2,2,2-Trifluoro-ethyl)-3,4,4a,5,7,8-hexahydro-1-thia-6-aza-cyclopenta[cd]azulene-6-carboxylic acid ethyl ester NaBH$_4$ (15 mg, 0.208 mmol) and a catalytic amount of acetic acid were added to the product from step (g) (72 mg, 0.208 mmol) in ethanol (3 mL) and the reaction was stirred at ambient temperature for 20 minutes. The reaction was quenched with acetic acid (dropwise) and partitioned between water and DCM. The organic layer was concentrated. Tin chloride dihydrate (187 mg, 0.832 mmol) was added to the crude product in acetic acid (2 mL) and the reaction was heated to 80° C. for 2 hours. Additional SnCl$_2$ was added (150 mg) and the reaction was heated for an additional 4 hours. The reaction was then diluted with water and extracted into DCM. The organic layer was concentrated to give the sub-title compound that was used without further purification.

i.) (R,S)-2-(2,2,2-Trifluoro-ethyl)-4,4a,5,6,7,8-hexahydro-3H-1-thia-6-aza-cyclopenta[cd]azulene TMSI (45 µL) was added to the product from step (h) in DCM (2 mL) and heated to 50° C. in the dark for 2 hours. The reaction was cooled to ambient temperature and quenched with methanol. The reaction was concentrated and purified by preparative LCMS to give the title compound. $^1$H NMR (CD$_3$OD) δ 3.58-3.71 (m, 2H), 3.51 (q, J=10.8 Hz, 2H), 3.07-3.16 (m, 3H), 2.99-3.04 (m, 4H), 1.91-2.07 (m, 2H). MS: ESI (positive): 262 (M+H).

Example 14

(R,S)-2-Bromo-3,3-dimethyl-4,4a,5,6,7,8-hexahydro-3H-1-thia-6-aza-cyclopenta[cd]azulene (Scheme 5)

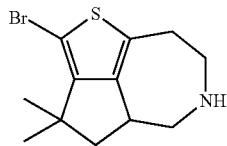

a.) (R,S)-3,3-Dimethyl-3,4,4a,5,7,8-hexahydro-1-thia-6-aza-cyclopenta[cd]azulene-6-carboxylic acid ethyl ester A solution of 2M Me$_2$Zn in toluene (1 mL) was added to TiCl$_4$ (380 mg, 2.02 mmol) in DCM at −78° C. and stirred for 10 minutes. The product from Example 13, step (d) (89 mg, 0.336 mmol) was added and the reaction was warmed to 0° C. and stirred cold for 1 hour. The reaction was quenched with water and extracted into DCM. The organic layer was concentrated to give the sub-title compound that was purified by preparative LCMS prior to use in subsequent steps. MS: ESI (positive): 280 (M+H).

b.) (R,S)-2-Bromo-3,3-dimethyl-3,4,4a,5,7,8-hexahydro-1-thia-6-aza-cyclopenta[cd]azulene-6-carboxylic acid ethyl ester The sub-title compound was prepared by the method of example 5, step (a) using the product from step (a) and was used in crude form without purification.

c.) (R,S)-2-Bromo-3,3-dimethyl-4,4a,5,6,7,8-hexahydro-3H-1-thia-6-aza-cyclopenta[cd]azulene The title compound was prepared by the method described in example 5, step (d) using the product from step (b) and purified by preparative HPLC-MS. $^1$H NMR (CD$_3$OD) δ 3.31-3.58 (m, 3H), 2.85-3.07 (m, 3H), 2.63 (t, J=10.5 Hz, 1H), 2.24 (dd, J=6.9 Hz, J=12.3 Hz, 1H), 1.86-1.95 (m, 1H), 1.44 (s, 3H) 1.26 (s, 3H). MS: ESI (positive): 288 (M+H).

Example 15

(R,S)-2-Bromo-5-methyl-5,6,7,8-tetrahydro-4H-thieno[2,3-d]azepine (Scheme 6)

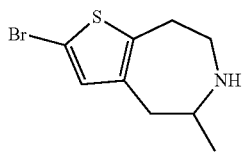

a.) (R,S)-5-Methyl-4-oxo-4,5,7,8-tetrahydro-thieno[2,3-d]azepine-6-carboxylic acid ethyl ester The product of Example 1, step (c) (1.06 g, 4.4 mmol) was dissolved in 20 mL THF and treated with LHMDS (5.3 mL of 1M in THF). After stirring for 1 hour at room temperature, MeI (326 uL, 5.3 mmol) was added and the reaction was stirred 1 hour at room temperature. The reaction was evaporated onto silica gel and purified by silica gel chromatography (10% to 30% EtOAc in hexanes) to give 175 mg of the sub-title compound.

b.) (R,S)-5-Methyl-4,5,7,8-tetrahydro-thieno[2,3-d]azepine-6-carboxylic acid ethyl ester The product of step (a) (75 mg, 0.30 mmol) was dissolved in DCE (3 mL) and treated with ZnI$_2$ (143 mg, 0.45 mmol) followed by NaCNBH3 (132 mg, 2.1 mmol). After stirring for 3 days at room temperature, the reaction was filtered and the filtrate was washed with DCM and discarded. The organic washes were combined, washed with water (2×10 mL), and dried over MgSO$_4$. Concentration gave 22 mg of a mixture of the sub-title compound and the alcohol corresponding to mono-reduction of the ketone starting material. The mixture was carried directly into the subsequent steps.

c.) (R,S)-2-Bromo-5-methyl-5,6,7,8-tetrahydro-4H-thieno[2,3-d]azepine

The product of step (b) (22 mg, 0.092 mmol) was dissolved in 2 mL of 1:1 HOAc:CHCl$_3$ and treated with NBS (25 mg, 0.14 mmol). After stirring for ½ hour, the reaction was concentrated to dryness and treated with 2 mL EtOH and 2 mL of 40% KOH. After heating to 100° C. for 24 hours and then to 120° C. for an additional 24 hours, the reaction was cooled, diluted with water, and extracted 3× with DCM. Purification by preparative HPLC-MS gave the title compound. MS: ESI (positive): 248 (M+H).

Example 16

4-Methyl-1-trifluoromethyl-1,2,3,4,5,6,7,8-octahydro-9-thia-6-aza-cyclopenta[a]azulene (Scheme 3)

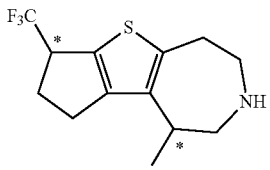 [SMILES: CC1CNCCc2sc3c(c21)CCC3C(F)(F)F]

a.) 4-Methyl-4,5,7,8-tetrahydro-thieno[2,3-d]azepine-6-carboxylic acid ethyl ester The product of Example 9, step (c) (enantiomer 2, 1.0 g, 2.51 mmol) was dissolved in 100 mL EtOH and treated with 1 g of Pd/C (wet, Degussa grade E101) and stirred rapidly under 1 atm of H$_2$ for 2 hours. The reaction was filtered through celite and concentrated to give 600 mg of the sub-title compound.

b.) 4-Methyl-2-(2,2,2-trifluoro-acetyl)-4,5,7,8-tetrahydro-thieno[2,3-d]azepine-6-carboxylic acid ethyl ester The product of step (a) was dissolved in DCE (100 mL) and treated with AlCl$_3$ (3.3 g, 25 mmol) followed by trifluoroacetic anhydride (3.5 mL, 25 mmol). After heating to 80° C. for 2 hours, another portion of AlCl$_3$ and trifluoroacetic anhydride was added (25 mmol each). After stirring for 1 hour at 80° C., the reaction was quenched over ice and carefully made basic by the cautious addition of Et$_3$N. The thick precipitate was filtered and discarded. The resulting mixture was extracted with DCM (3×100 mL). After concentration of the extracts to approximately 100 mL, 0.5 mL each of ethyl chloroformate and DIEA was added. After stirring for ½ hour, the solution was washed with water, concentrated and purified by silica gel chromatography (25% EtOAc/Hex) to give 460 mg of the sub-title compound.

c.) 2-(1-Carboxymethyl-2,2,2-trifluoro-ethyl)-4-methyl-4,5,7,8-tetrahydro-thieno[2,3-d]azepine-6-carboxylic acid ethyl ester The product of step (b) (460 mg, 1.37 mmol) was dissolved in 25 mL THF and treated with triethylphosphonoacetate (550 uL, 2.74 mmol) and LHMDS (2.2 mL of 1M in THF). After stirring for 15 minutes, the reaction was quenched with water (100 mL) and the product was extracted into DCM (2×50 mL). After drying the extracts over MgSO$_4$ and concentration, the crude residue was dissolved in EtOH (50 mL) and treated with 300 mg Pd/C (10%, wet, Degussa grade E101). After stirring under 1 atm of H$_2$ for 2 hours, the reaction was filtered through celite and treated with 1M NaOH (10 mL). After stirring overnight at room temperature, the reaction was acidified with 1M HCl and the product was extracted into DCM (2×25 mL). The extracts were dried over MgSO$_4$ and concentrated to give 0.5 g of the sub-title compound, which was used without further purification.

d.) 4-Methyl-3-oxo-1-trifluoromethyl-2,3,4,5,7,8-hexahydro-1H-9-thia-6-aza-cyclopenta[a]azulene-6-carboxylic acid ethyl ester The product of step (c) (500 mg, 1.3 mmol) was dissolved in DCM (20 mL) and treated with DMF (50 uL) followed by oxalyl chloride (240 uL, 1.45 mmol). After stirring for ½ hour, an additional quantity of oxalyl chloride (240 uL) was added. After stirring for an additional 1 hour, the reaction was concentrated to dryness and the residue was re-dissolved in DCM (5 mL). AlCl$_3$ (360 mg, 2.7 mmol) was added and the reaction was stirred for 1 hour at room temperature. The reaction was quenched with ice water (10 mL) and the product was extracted into DCM/EtOH (4:1, 2×30 mL). The extracts were dried over MgSO$_4$ and concentrated to give 468 mg of the sub-title compound, which was used without further purification. The diastereomers could be separated by silica gel chromatography (25% to 35% EtOAc in Hex) to give diastereomer 1 (top spot, first eluting product) and diastereomer 2 (bottom spot, second eluting product).

e.) 4-Methyl-1-trifluoromethyl-2,3,4,5,7,8-hexahydro-1H-9-thia-6-aza-cyclopenta[a]azulene-6-carboxylic acid ethyl ester The product of step (d) (mixture of diastereomers, 234 mg, 1.54 mmol) was dissolved in 5 mL EtOH and treated with NaBH$_4$ (117 mg, 3.1 mmol). After stirring for 15 minutes, the reaction was quenched with HOAc and diluted with water (10 mL). The product was extracted into DCM (2×25 mL) and the extracts were concentrated to dryness. The crude residue was dissolved in HOAc (8 mL) and concentrated HCl (4 mL) and treated with SnCl$_2$ (1.4 g, 6.2 mmol). After heated to 80° C. for 1 hour, the reaction was cooled and diluted with water (15 mL). The product was extracted into DCM (3×25 mL) and the extracts were dried over MgSO$_4$ and concentrated to dryness. The diastereomers were separated by HPLC (Novapak C-18, 19×300 mm, 55% CH$_3$CN/water, 10 mL/min) to give diastereomer 1 (rt=23.0 min) and diastereomer 2 (rt=24.2 min) giving approximately 20 mg of each diastereomer.

f.) 4-Methyl-1-trifluoromethyl-1,2,3,4,5,6,7,8-octahydro-9-thia-6-aza-cyclopenta[a]azulene The product of step (e) (diastereomer 1 and diastereomer 2, separately, 20 mg, 0.06 mmol) was dissolved in 3 mL CHCl$_3$ and treated with TMSI (40 uL, 0.29 mmol). After heating to 70° C. overnight, the reaction was quenched with MeOH (5 mL) and 1 M NaOH (2 mL). The title compound was extracted into CHCl$_3$ (2×10 mL) and subsequently purified by preparative HPLC-MS.

Diastereomer 1: $^1$H NMR (CD$_3$OD) δ 4.01-3.90 (m, 1H), 3.43-2.95 (m, 8H), 2.87-2.64 (m, 3H), 2.56-2.44 (m, 1H), 1.33-1.31 (m, 3H). MS: ESI (positive): 276 (M+H).

Diastereomer 2: $^1$H NMR (CD$_3$OD) δ 4.01-3.90 (m, 1H), 3.42-2.94 (m, 8H), 2.84-2.64 (m, 3H), 2.55-2.45 (m, 1H), 1.32-1.29 (m, 3H). MS: ESI (positive): 276 (M+H).

Example 17

3,3,4-Trimethyl-1-trifluoromethyl-1,2,3,4,5,6,7,8-octahydro-9-thia-6-aza-cyclopenta[a]azulene
(Scheme 3)

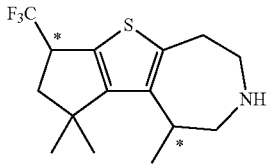

DCM (5 mL) was cooled to −78° C. and treated with TiCl$_4$ (91 uL, 0.83 mmol) and Me$_2$Zn (0.4 mL of 2M in toluene). After stirring for 10 minutes, the product of Example 16,[1] step (d) (diastereomer 1 and diastereomer 2, separately, 50 mg each, 0.14 mmol) was dissolved in 5 mL DCM and added to the resulting dark slurry. The reaction was warmed to room temperature and stirred for 3 days. The reaction was quenched over ice and the product was extracted into DCM (2×15 mL). After drying over MgSO$_4$, the extracts were concentrated, re-dissolved in CHCl$_3$ (10 mL), and treated with TMSI (80 uL, 0.58 mmol). The reaction was heated overnight to 70° C. and subsequently quenched with MeOH (5 mL) and 1 M NaOH (2 mL). The title compound was extracted into CHCl$_3$ (2×10 mL) and purified by preparative HPLC-MS.

[1] The original "Examples" referred to Example 28, which is clearly a typo since there are only 19 example. We think it should be Example 16, but we are not 100% sure.

Diastereomer 1: $^1$H NMR (CD$_3$OD) δ 4.20-3.89 (m, 1H), 3.49-3.34 (m, 3H), 3.28-3.89 (m, 4H), 2.54 (dd, J=9.3, 13.8 Hz, 1H), 2.32 (dd, J=5.4, 13.5 Hz, 1H), 1.39 (s, 3H), 1.35 (s, 3H), 1.34 (d, J=6.3 Hz, 3H). MS: ESI (positive): 304 (M+H).

Diastereomer 2: $^1$H NMR (CD$_3$OD) δ 3.98 (sext., J=8.1 Hz, 1H), 3.52-3.34 (m, 3H), 3.27-2.88 (m, 4H), 2.46 (dd, J=8.4, 13.2 Hz, 1H), 2.33 (dd, J=6.0, 13.5 Hz, 1H), 1.42 (s, 3H), 1.38-1.33 (m, 3H), 1.29 (s, 3H). MS: ESI (positive): 304 (M+H).

Example 18

2,2-Dimethyl-1-(5,6,7,8-tetrahydro-4H-thieno[2,3-d] azepin-2-yl)-propan-1-one (Scheme 1)

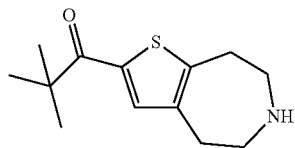 [SMILES: CC(C)(C)C(=O)c1cc2c(s1)CCNCC2]

a.) 2-(2,2-Dimethyl-propionyl)-4,5,7,8-tetrahydro-thieno[2,3-d]azepine-6-carboxylic acid ethyl ester A solution of the product from Example 1, step (d) (160 mg, 0.71 mmol) in dichloroethane (5 ml) at 0° C. was treated with trimethyl acetyl chloride (0.17 ml, 1.42 mmol) and AlCl$_3$ (190 mg, 1.42 mmol). The reaction mixture was allowed to stir at 0° C. for 30 minutes and then allowed to warm to room temperature. The reaction mixture was quenched by the addition of saturated solution of NaHCO$_3$ (30 ml) and extracted with dichloromethane (3×30 ml). The combined organic extracts were washed with brine (50 ml), dried (MgSO$_4$), and solvent evaporated in vacuo to give a tan oil. The crude oil was purified by silica gel chromatography (0% to 50% EtOAc in Hex) to give the subtitle compound as a clear oil (60 mg, 27%). MS: ESI (positive): 310 (M+H).

b.) 2,2-Dimethyl-1-(5,6,7,8-tetrahydro-4H-thieno[2,3-d]azepin-2-yl)-propan-1-one A solution of the product from step a) (50 mg, 0.16 mmol) in methanol (5 ml) was treated with Ba(OH)$_2$ (200 mg, 1.2 mmol). The reaction mixture was heated in a sealed tube for 30 hours and then allowed to cool to room temperature. The reaction mixture was concentrated in vacuo and neutralized by the addition of 1N HCl. An aliquot of this solution was purified by preparative HPLC-MS to give the title compound that was converted into its HCl salt. $^1$H NMR (300 MHz, DMSO-d$_6$) δ 9.62 (br s, 2H); 7.81 (s, 1H); 3.08-3.23 (m, 8H); 1.30 (s, 9H); MS: ESI (positive): 238 (M+H).

Example 19

1-(3-Chloro-5,6,7,8-tetrahydro-4H-thieno[2,3-d] azepin-2-yl)-2,2-dimethyl-propan-1-one (Scheme 7)

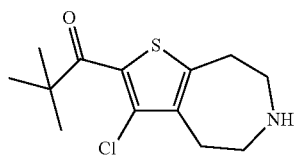

a.) (4,5-Dichloro-thiophen-2-yl)-oxo-acetic acid ethyl ester

At 5-10° C., Chloro-oxo-acetic acid ethyl ester (5.43 ml, 48.7 mmol) was added to 2,3-Dichlorothiophene (5 g, 32.6 mmol). A solution of AlCl$_3$ (6.49 g, 48.7 mmol) dissolved in nitromethane (13 ml) was added dropwise such that the internal reaction temperature did not rise above 10° C. After 1 hour, the reaction mixture was poured into ice water and extracted with CH$_2$Cl$_2$ (2×100 ml). The organic layer was washed with 10% NaHCO$_3$ (2×50 ml), water (1×50 ml) and brine (1×50 ml). Drying (Na$_2$SO$_4$) and concentration provided a light orange solid that was purified by silica gel chromatography (EtOAc/hexane-gradient) providing 6.8 g (82%) of the subtitle compound.

b.) (4,5-Dichloro-thiophen-2-yl)-hydroxy-acetic acid ethyl ester

A solution of the product from step a) (23.0 g, 90.9 mmol) in THF (500 ml) was treated with NaBH(OAc)$_3$ (23.1 g, 109 mmol) and AcOH (250 µl) at 60° C. for 1 hour. The reaction was quenched with AcOH (8 ml) and concentrated to ~250 ml. The contents were diluted with H$_2$O (400 ml) and extracted with CH$_2$Cl$_2$ (1×400 ml; 1×100 ml). The organic layer was dried (MgSO$_4$) and concentrated providing 23 g of the subtitle compound. $^1$H NMR (300 MHz, CDCl$_3$) δ 6.91 (s, 1H); 5.25 (dd, J$_1$=6 Hz, J$_2$=1 Hz, 1H); 4.22-4.40 (m, 2H); 3.52-3.60 (br m, 1H); 1.33 (t, J=7 Hz, 3H).

c.) (4,5-Dichloro-3-methoxycarbonylmethyl-thiophen-2-yl)-acetic acid ethyl ester A solution of the product from step (b) (12.2 g, 48.0 mmol) in decalin (145 ml) was treated with trimethylorthoacetate (24.5 ml, 192 mmol) and hexanoic acid (0.61 ml). The flask was equipped with a vigreux column and heated to 180° C. Additional hexanoic acid (3 ml) was periodically added over 6 h and the reaction was heated overnight. The reaction was concentrated on the rotavap and the residue was extracted with MeOH (100 ml×2). The MeOH extracts were concentrated and purified by silica gel chromatography (EtOAc/Hexane-gradient) providing 4.36 g (29%) of the subtitle compound. MS: ESI (positive): 311, 313 (M+H).

d.) (3-Carboxymethyl-4,5-dichloro-thiophen-2-yl)-acetic acid

A solution of the product from step (c) (1.14 g, 3.66 mmol) in MeOH (7 ml) at 0° C. was treated dropwise with 2M NaOH (3.8 ml). The reaction was warmed to 22° C. and stirred overnight. The solvent was evaporated and the residue was dissolved in 2 M NaOH (50 ml) and extracted with ether (2×50 ml). The basic layer was cooled to 0° C. and acidified to pH 1 with 6 M HCl. The acidic layer was back extracted EtOAc (4×100 ml) and the organic layer was dried (MgSO$_4$) and concentrated. The crude solid was triturated with hexanes and filtered providing 2.75 g (73%) of the subtitle compound. MS: ESI (negative): 267, 269 (M−H).

e.) 2-[4,5-Dichloro-3-(2-hydroxy-ethyl)-thiophen-2-yl]-ethanol

A solution of the product from step (d) (2.5 g, 9.33 mmol) in THF (85 ml) was cooled to 0° C. and a 1M solution of BH$_3$-THF (46.6 ml, 46.6 mmol) was added dropwise over 10 min. and stirred for an additional 20 minutes after the addition was complete. The reaction was warmed to 22° C. and stirred for 2 hours. The reaction was poured into ice cold sat. NaHCO$_3$ (150 ml) and extracted with EtOAc. The crude was passed through a plug of silica gel washing with EtOAc. Concentration of the eluent provided 1.99 g (88%) of the subtitle compound.

f.) Methanesulfonic acid 2-[4,5-dichloro-2-(2-methanesulfonyloxy-ethyl)-thiophen-3-yl]-ethyl ester A solution of the product from step (e) (1.99 g, 8.25 mmol) in CH$_2$Cl$_2$ (41 ml) was cooled to 0° C. and treated with triethylamine (3.4 ml, 24.7 mmol) followed by dropwise addition of methanesulfonyl chloride (1.4 ml, 18.1 mmol) over 10 min. After 45 minutes, the crude reaction was diluted with CH$_2$Cl$_2$ (100 ml) and washed with ice water (25 ml), 10% citric acid (2×25 ml), sat. NaHCO$_3$ (2×25 ml) and brine (1×25 ml). The organic layer was dried (MgSO$_4$), concentrated to 20 ml and diluted with anhydrous dioxane (76 ml). This mixture was concentrated to remove remaining CH$_2$Cl$_2$ and the resulting dioxane solution was carried forward to the next reaction.

g.) 6-Benzyl-2,3-dichloro-5,6,7,8-tetrahydro-4H-thieno[2,3-d]azepine

The bismesylate dioxane solution generated in step (f) was transferred to a 3-neck reaction flask equipped with a dropping funnel and condenser Anhydrous potassium carbonate (4.93 g, 35.7 mmol) was added and the contents were heated to reflux. Next, a solution of benzylamine (2.71 g, 25.3 mmol) in anhydrous dioxane (27 ml) was added dropwise over 45 minutes and heating was continued for 16 hours. The salts were filtered off and the solvent was concentrated. The crude was purified by silica gel chromatography (EtOAc/Hexane-gradient) providing 1.43 g (62%) of the subtitle compound. $^1$H NMR (300 MHz, CDCl$_3$) δ 7.20-7.40 (m, 5H); 3.73 (s, 2H); 2.68-2.89 (m, 8H); MS: ESI (positive): 312, 314 (M+H).

h.) 1-(6-Benzyl-3-chloro-5,6,7,8-tetrahydro-4H-thieno[2,3-d]azepin-2-yl)-2,2-dimethyl-propan-1-one The product from step (g) (109 mg, 0.35 mmol) in anhydrous THF (5 ml) was cooled to −78° C. under a nitrogen atmosphere and treated with 1.6 M n-butyl lithium in hexane (0.25 ml). The reaction mixture was stirred at −78° C. for 5 minutes followed by the addition of trimethyl acetyl chloride (0.22 ml, 1.75 mmol). After 10 additional minutes at −78° C., the reaction mixture was allowed to warm to room temperature. The reaction was quenched with saturated NaHCO$_3$ (20 ml) and extracted with ethyl acetate (3×20 ml). The combined organic extracts were washed with brine (50 ml), dried (MgSO$_4$), and solvent evaporated in vacuo to give the subtitled compound as an orange oil which was used in the next step without further purification. MS: ESI (positive): 362, 364 (M+H).

i.) 1-(3-Chloro-5,6,7,8-tetrahydro-4H-thieno[2,3-d]azepin-2-yl)-2,2-dimethyl-propan-1-one A solution of the product from step (h) (assumed 0.35 mmol) in anhydrous dichloroethane (2 ml) was cooled to 0° C., treated with K$_2$CO$_3$ (~50 mg) and 1-chloroethyl chloroformate (0.38 ml, 3.5 mmol). The reaction was allowed to warmed to 22° C. for 18 hours. The reaction diluted with CH$_2$Cl$_2$ (50 ml) and washed with sat. NaHCO$_3$ (2×50 ml), brine (50 ml), dried (MgSO$_4$) and solvent evaporated in vacuo providing an oily residue, which was dissolved in anhydrous MeOH (10 ml) and refluxed for 1.5 hours. The MeOH was evaporated in vacuo to give the crude product. A portion of the crude was purified by preparative HPLC-MS to give the title compound. $^1$H NMR (300 MHz, CDCl$_3$) δ 6.25 (br s, 1H); 3.05-3.19 (m, 8H); 1.34 (s, 9H); MS: ESI (positive): 272, 274 (M+H).

The following procedure was utilized to evaluate representative compounds of the present invention as 5HT$_{2c}$ receptor agonists. The results of this assay are set forth in Table 1.

Cell Culture

HEK 293 EBNA expressing the human 5HT$_{2c}$ receptor (VNV Isoform) (Burns et al., NATURE 387:30308, 1997 Fitzgerald et al., NEUROPSYCHO-PHARMACOLOGY 21:825-905, 1999) were grown in DMEM containing 10% dialysed FBS, 9 μg/ml blasticidin at 37° C. in 5% CO$_2$ atmosphere.

Calcium Mobilization

HEK 293 EBNA cells expressing human 5HT$_{2c}$ receptor (2×10$^4$/well) were seeded in black 384-well collagen coated plates and incubated overnight at 37° C. in a 5% CO2/95% atmosphere. After removing medium, cells were treated with HBSS buffer (137 mM NaCl, 5.4 mM KCl, 5.5 mM Glucose, 20 mM Hepes, pH 7.5, 2.1 mM MgCl$_2$, 0.3 mM CaCl$_2$, 0.02 mM MgSO$_4$, 3.0 mM NaHCO$_3$, and 0.64 mM KH$_2$PO$_4$) containing the Calcium3 dye (Molecular Device, CA), 2.5 mM probenecid and 0.08% pluronic acid for 60 minutes according to manufacturer's instruction. Compounds were diluted in CsCl Ringers buffer (58.3 mM CsC1, 5.4 mM KCl, 5.5 mM Glucose, 20 mM Hepes, pH 7.5, 2.1 mM MgCl$_2$, 1.2 mM CaCl$_2$). 5HT was utilized as a positive control. Ligand-induced calcium release and consequent fluorescence was measured on a Fluorometric Imaging Plate Reader (FLIPR, Molecular Device, CA).

Data Analysis

All data were analyzed by nonlinear least square curve fitting using Prism 4.0 software. Agonist stimulation of calcium-induced fluorescence in FLIPR was fitted to sigmoidal dose response using equation Y=Bottom+(Top−Bottom)/(1+ 10^((Log EC50−X))), where X is the logarithm of concentration of compounds and Y is the fluorescent response.

TABLE 1

| Example Number | 5-HT2c EC50 (hVNV, μM) |
|---|---|
| 1 | <0.1 |
| 2 | <0.01 |
| 3 | <0.01 |
| 4 | <0.01 |
| 5 | <0.01 |
| 6 | <0.01 (for both enantiomers) |
| 7 | <1 (for both enantiomers) |
| 8 | <0.1 |
| 9 | <0.1 (for both enantiomers) |
| 10 | <0.1 (for both enantiomers) |
| 11 | <0.1 |
| 12 | <0.1 |
| 13 | <0.1 |
| 14 | <1 |
| 15 | <1 |
| 16 | <0.1 (for both enantiomers) |
| 17 | Diastereomer 1 < 0.1 |
|  | Diastereomer 2 < 1 |
| 18 | <0.01 |
| 19 | <0.1 |

What is claimed is:

1. A compound selected from the group consisting of:
3-Bromo-2-(2,2,2-trifluoro-ethyl)-5,6,7,8-tetrahydro-4H-thieno[2,3-d]azepine;
(R,S)-2-(2,2,2-Trifluoro-1-methyl-ethyl)-5,6,7,8-tetrahydro-4H-thieno[2,3-d]azepine;
2-(2,2,2-Trifluoro-1,1-dimethyl-ethyl)-5,6,7,8-tetrahydro-4H-thieno[2,3-d]azepine;
3-Bromo-4-methyl-2-(2,2,2-trifluoro-ethyl)-5,6,7,8-tetrahydro-4H-thieno[2,3-d]azepine;
(R,S)-2-(2,2,2-Trifluoro-ethyl)-4,4a,5,6,7,8-hexahydro-3H-1-thia-6-aza-cyclopenta[cd]azulene; and
or a pharmaceutically acceptable salt thereof.

2. A pharmaceutical composition comprising at least one compound of claim 1 and a pharmaceutically acceptable carrier.

3. A method of treating a disease, disorder and/or condition selected from obesity, type II diabetes, obsessive compulsive disorder, depression, epilepsy and schizophrenia in a patient comprising administering an effective amount of at least one compound of claim 1.

* * * * *